(12) United States Patent
Akahori

(10) Patent No.: US 12,159,448 B2
(45) Date of Patent: Dec. 3, 2024

(54) LEARNING IMAGE GENERATION DEVICE, LEARNING IMAGE GENERATION METHOD, LEARNING IMAGE GENERATION PROGRAM, LEARNING METHOD, LEARNING DEVICE, AND LEARNING PROGRAM

(71) Applicant: FUJIFILM Corporation, Tokyo (JP)

(72) Inventor: Sadato Akahori, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 446 days.

(21) Appl. No.: 17/584,289

(22) Filed: Jan. 25, 2022

(65) Prior Publication Data

US 2022/0148294 A1 May 12, 2022

Related U.S. Application Data

(63) Continuation of application No. PCT/JP2020/028685, filed on Jul. 27, 2020.

(30) Foreign Application Priority Data

Jul. 26, 2019 (JP) ................ 2019-138235

(51) Int. Cl.
*G06V 10/774* (2022.01)
*G06T 7/00* (2017.01)
*G06V 10/75* (2022.01)

(52) U.S. Cl.
CPC ........ *G06V 10/7747* (2022.01); *G06T 7/0014* (2013.01); *G06V 10/751* (2022.01); *G06T 2207/10081* (2013.01)

(58) Field of Classification Search
CPC .............. G06V 10/7747; G06V 10/751; G06T 7/0014; G06T 2207/100081
See application file for complete search history.

(56) References Cited

U.S. PATENT DOCUMENTS

| 2008/0292194 A1* | 11/2008 | Schmidt | G06T 7/0012 |
| | | | 382/131 |
| 2009/0169075 A1 | 7/2009 | Ishida et al. | |
| 2013/0202177 A1* | 8/2013 | Bar-Aviv | G06T 19/20 |
| | | | 382/128 |

(Continued)

FOREIGN PATENT DOCUMENTS

| JP | 2018206382 | 12/2018 |
| JP | 2019028650 | 2/2019 |
| WO | 2007029467 | 3/2007 |

OTHER PUBLICATIONS

"Office Action of Japan Counterpart Application", issued on Jan. 17, 2023, with English translation thereof, pp. 1-3.

(Continued)

*Primary Examiner* — Myron Wyche
(74) *Attorney, Agent, or Firm* — JCIPRNET

(57) ABSTRACT

A learning image generation device includes an image acquisition unit that acquires a learning image, and a variation learning image generation unit that generates a variation learning image by adding a variation in which an output of a model deviates from a target value to a pixel value of at least one pixel that constitutes the learning image in a case in which the learning image acquired by the image acquisition unit is input to the model.

19 Claims, 16 Drawing Sheets

(56) References Cited

U.S. PATENT DOCUMENTS

2018/0349759 A1 12/2018 Isogawa et al.
2019/0197358 A1 6/2019 Madani et al.

OTHER PUBLICATIONS

"International Search Report (Form PCT/ISA/210) of PCT/JP2020/028685," mailed on Oct. 13, 2020, with English translation thereof, pp. 1-4.
"Written Opinion of the International Searching Authority (Form PCT/ISA/237)" of PCT/JP2020/028685, mailed on Oct. 13, 2020, with English translation thereof, pp. 1-6.

* cited by examiner

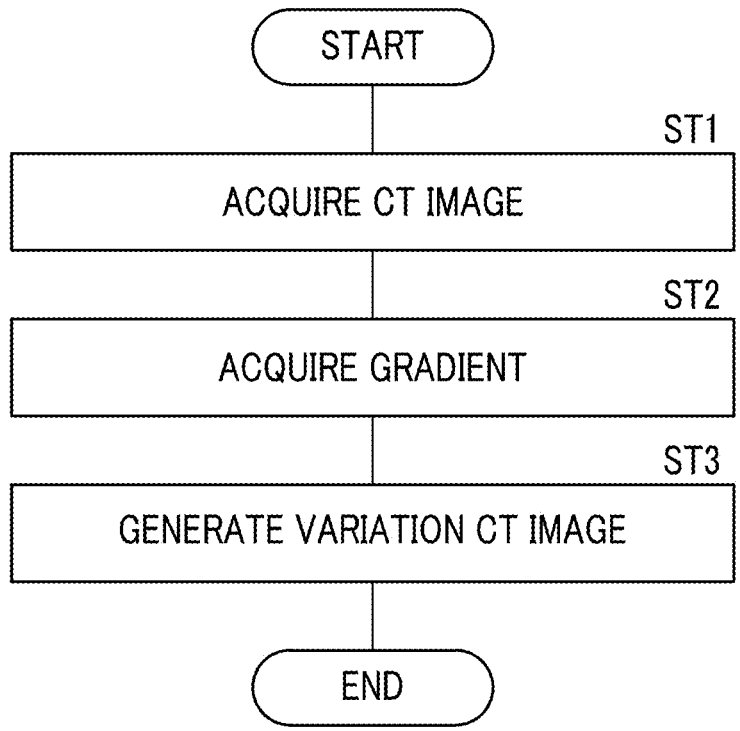
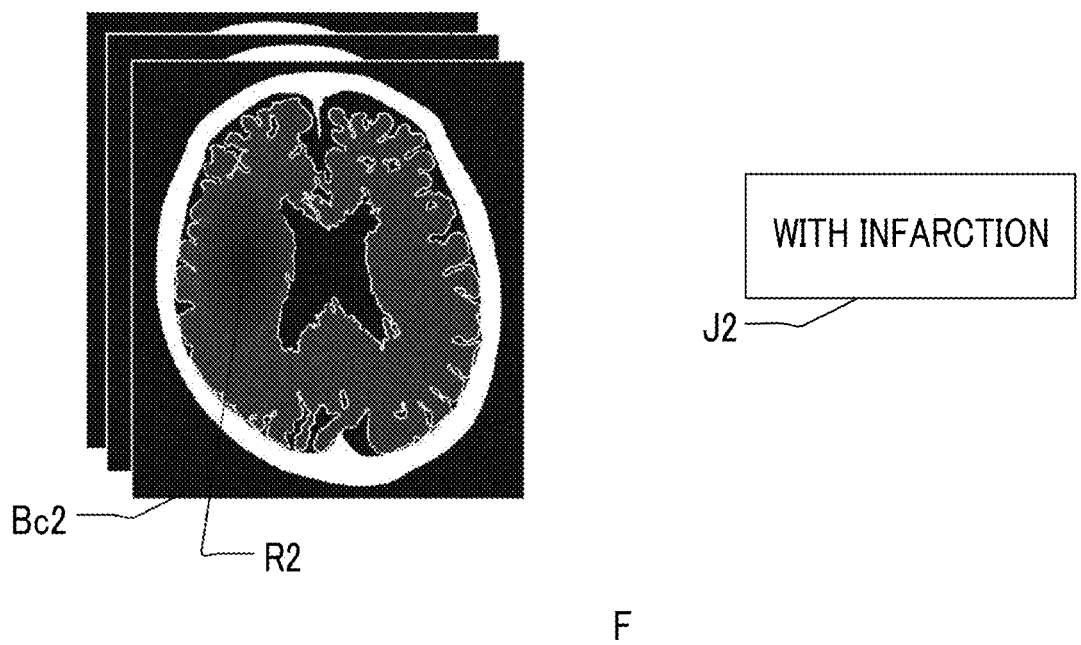

F-2

LEARNING IMAGE GENERATION DEVICE, LEARNING IMAGE GENERATION METHOD, LEARNING IMAGE GENERATION PROGRAM, LEARNING METHOD, LEARNING DEVICE, AND LEARNING PROGRAM

CROSS-REFERENCE TO RELATED APPLICATIONS

This application is a continuation application of International Application No. PCT/JP2020/028685, filed on Jul. 27, 2020, which is incorporated herein by reference in its entirety. Further, this application claims priority from Japanese Patent Application No. 2019-138235, filed on Jul. 26, 2019, the disclosure of which is incorporated by reference herein.

BACKGROUND

Technical Field

The present disclosure relates to a learning image generation device, a learning image generation method, a learning image generation program, a learning method, a learning device, and a learning program.

Related Art

Machine learning technology using deep learning has been attracting attention in recent years. It is known that it is possible to, by using deep learning, construct a model for detecting and classifying an object included in an image and segmenting a region of the object included in the image. In deep learning, various technologies have been developed to further improve the accuracy of image identification. JP 2019-28650 A discloses an image identification device that acquires an input image based on a sensor value of an imaging apparatus and identifies the input image based on the acquired sensor value by using an identifier having a conversion unit. The image identification device can obtain an image suitable for identification by learning the conversion unit based on a learning image based on the sensor value of the imaging apparatus and correct data given to the learning image, and can realize the image identification with high accuracy.

Generally, in deep learning, it is known that a more accurate output result can be obtained as the number of the learning images is larger. However, in a case in which an image to be input is, for example, a brain image of a brain that has developed a cerebral apoplexy, such as subarachnoid hemorrhage, intracerebral hemorrhage, and cerebral infarction, a shape, a size, and a developing location of a diseased region, such as an infarcted region and a bleeding region, to be segmented are undefined. In addition, a pixel value of the diseased region in the brain image is changed in response to the elapsed time from the development of the disease. Therefore, there are various cases in the brain image, and it is difficult to prepare the learning image that can cover all of various cases. In addition, in a case in which the learning image that can cover all of various cases cannot be prepared, it is difficult to stably operate the model for an unknown image in which the learning image is not present.

SUMMARY

The present disclosure provides a learning image generation device, a learning image generation method, a learning image generation program, a learning method, a learning device, and a learning program which can learn a model to be stably operated by using a limited learning image.

A first aspect of the present disclosure relates to a learning image generation device comprising an image acquisition unit that acquires a learning image, and a variation learning image generation unit that generates a variation learning image by adding a variation in which an output of a model deviates from a target value to a pixel value of at least one pixel that constitutes the learning image in a case in which the learning image acquired by the image acquisition unit is input to the model.

Here, for example, in a case in which the learning image is a brain image, the model (classification discrimination model) is used, which is discriminated that there is no cerebral infarction in a case in which the output of the model is 0 or more and less than 0.5 and discriminated that there is a cerebral infarction in a case in which the output of the model is 0.5 or more and 1 or less. In this case, in a case in which the output of the model is 0.6 for the learning image before the variation, the learning image is an image with the infarction. Since this image is the image with the infarction, "1" discriminated to have the highest possibility of having the infarction is the "target value" of the present disclosure. Therefore, the "variation deviating the target value" is a variation having a value at which the output of the model further deviates from "1", the value being 0.5 or more and less than 0.6. On the other hand, in a case in which the output of the model is 0.3 for the learning image before the variation, the learning image is an image without the infarction. Since this image is the image without the infarction, "0" discriminated to have the highest possibility of having no infarction is the "target value" of the present disclosure. Therefore, the "variation deviating from the target value" is a variation having a value at which the output of the model further deviates from "0", the value being more than 0.3 and less than 0.5.

In addition, for example, in a case in which the learning image is the brain image, the model that performs output for each pixel that constitutes the learning image, specifically, the model (segmentation discrimination model) is used in which it is discriminated that the pixel does not belong to the cerebral infarcted region in a case in which the output of the model is 0 or more and less than 0.5 and the pixel belongs to the cerebral infarcted region in a case in which the output of the model is 0.5 or more and 1 or less. In this case, in a case in which the output of the model is 0.6 for one pixel that constitutes the learning image before the variation, this pixel is the pixel belonging to the infarcted region. Since this pixel is the pixel belongs to the infarcted region, "1" discriminated to have the highest possibility of belonging to the infarcted region is the "target value" of the present disclosure. Therefore, the "variation deviating the target value" is a variation having a value at which the output of the model further deviates from "1", the value being 0.5 or more and less than 0.6. On the other hand, in a case in which the output of the model is 0.3 for one pixel that constitutes the learning image before the variation, this pixel is the pixel that does not belong to the infarcted region. Since this pixel is the pixel that does not belong to the infarcted region, "0" discriminated to have the highest possibility of not belonging to the infarcted region is the "target value" of the present disclosure. Therefore, the "variation deviating from the target value" is a variation having a value at which the output of the model further deviates from "0", the value being more than 0.3 and less than 0.5.

In a second aspect of the present disclosure, according to the first aspect, the variation learning image generation unit may acquire a gradient of an output value with respect to the pixel value of each pixel that constitutes the learning image, and adds the variation by using the acquired gradient.

In a third aspect of the present disclosure, the learning image generation device according to the aspect described above may further comprising a supervised data acquisition unit that acquires supervised data including the learning image and a correct learning image in which a correct region is defined in the learning image as a pair, in which the variation learning image generation unit determines an attention pixel by using the correct learning image in the supervised data acquired by the supervised data acquisition unit, acquires a gradient of an output value of the determined attention pixel, and adds the variation by using the acquired gradient.

In a fourth aspect of the present disclosure, according to the third aspect, the variation learning image generation unit may determine the pixel in the learning image corresponding to a pixel belonging to the correct region as the attention pixel.

In a fifth aspect of the present disclosure, according to the third or fourth aspect, the variation learning image generation unit may determine the pixel in the learning image corresponding to a pixel belonging to a region other than the correct region as the attention pixel.

In a sixth aspect of the present disclosure, according to any one of the third to fifth aspects, the variation learning image generation unit may determine the pixel in the learning image corresponding to a pixel belonging to a centroid of the correct region as the attention pixel.

In a seventh aspect of the present disclosure, according to the aspect described above, the model may be a model having a plurality of output units that classifies the input learning image into a plurality of classes including one or more correct classes, and the variation learning image generation unit may acquire a gradient of an output value output from the output unit that performs classification into the correct classes.

An eighth aspect of the present disclosure relates to a learning image generation method comprising acquiring a learning image, and generating a variation learning image by adding a variation in which an output of a model deviates from a target value to a pixel value of at least one pixel that constitutes the learning image in a case in which the acquired learning image is input to the model.

A ninth aspect of the present disclosure relates to a learning image generation program causing a computer to function as an image acquisition unit that acquires a learning image, and a variation learning image generation unit that generates a variation learning image by adding a variation in which an output of a model deviates from a target value to a pixel value of at least one pixel that constitutes the learning image in a case in which the learning image acquired by the image acquisition unit is input to the model.

Another aspect of the present disclosure relates to a learning image generation device comprising a memory that stores a command to be executed by a processor, and the processor configured to execute the stored command, in which the processor executes a process of acquiring a learning image, and generating a variation learning image by adding a variation in which an output of a model deviates from a target value to a pixel value of at least one pixel that constitutes the learning image in a case in which the acquired learning image is input to the model.

A tenth aspect of the present disclosure relates to a learning method comprising learning a model by using one or more first supervised data including a learning image and correct information in the learning image as a pair, and one or more second supervised data including one or more variation learning images generated by adding a variation in which an output of the model deviates from a target value to a pixel value of at least one pixel that constitutes the learning image in a case in which the learning image is input to the model, and the correct information in the learning image before the variation in each of the one or more variation learning images as a pair.

In an eleventh aspect of the present disclosure, according to the tenth aspect, the correct information may be a correct learning image in which a correct region is defined in the learning image.

In a twelfth aspect of the present disclosure, according to the tenth or eleventh aspect, the model may be learned by using a plurality of the first supervised data in first learning, and the model may be learned by replacing at least one first supervised data among the plurality of first supervised data with the second supervised data in second and subsequent learning.

In a thirteenth aspect of the present disclosure, according to the tenth or eleventh aspect, the model may be learned by using a plurality of the first supervised data in first learning, and the model may be learned by adding at least one second supervised data in second and subsequent learning.

In a fourteenth aspect of the present disclosure, according to the twelfth or thirteenth aspect, at least one of the second supervised data to be used or the number of the second supervised data may be randomly set for each learning in the second and subsequent learning.

In a fifteenth aspect of the present disclosure, according to the twelfth or thirteenth aspect, at least one of the second supervised data to be used or the number of the second supervised data may be set in advance in the second and subsequent learning.

In a sixteenth aspect of the present disclosure, according to any one of the twelfth to fifteenth aspects, the model may be learned by using only the plurality of first supervised data at least once in the second and subsequent learning.

A seventeenth aspect of the present disclosure relates to a learning device comprising a supervised data acquisition unit that acquires one or more first supervised data including a learning image and correct information in the learning image as a pair, and one or more second supervised data including one or more variation learning images generated by adding a variation in which an output of a model deviates from a target value to a pixel value of at least one pixel that constitutes the learning image in a case in which the learning image is input to the model, and the correct information in the learning image before the variation in each of the one or more variation learning images as a pair, and a learning unit that learns the model by using the one or more first supervised data and the one or more second supervised data acquired by the supervised data acquisition unit.

Another aspect of the present disclosure relates to a learning device comprising a memory that stores a command to be executed by a processor and the processor configured to execute the stored command, in which the processor execute a process of learning a model by using one or more first supervised data including a learning image and correct information in the learning image as a pair, and one or more second supervised data including one or more variation learning images generated by adding a variation in which an output of the model deviates from a target value to a pixel value of at least one pixel that constitutes the learning image in a case in which the learning image is input to the model, and the correct information in the learning image before the variation in each of the one or more variation learning images as a pair.

In an eighteenth aspect of the present disclosure, according to the seventeenth aspect, the learning unit may learn the model by the learning method according to any one of the tenth to sixteenth aspects.

A nineteenth aspect of the present disclosure relates to a learning program causing a computer to function as a supervised data acquisition unit that acquires one or more first supervised data including a learning image and correct information in the learning image as a pair, and one or more second supervised data including one or more variation learning images generated by adding a variation in which an output of a model deviates from a target value to a pixel value of at least one pixel that constitutes the learning image in a case in which the learning image is input to the model, and the correct information in the learning image before the variation in each of the one or more variation learning images as a pair, and a learning unit that learns the model by using the one or more first supervised data and the one or more second supervised data acquired by the supervised data acquisition unit.

Note that the learning device and the learning program of the present disclosure, the correct information may be the correct learning image in which the correct region is defined in the learning image.

According to the aspects described above, the present disclosure provides the learning image generation device, the learning image generation method, the learning image generation program, the learning method, the learning device, and the learning program which can learn the model to be stably operated by using a limited learning image.

BRIEF DESCRIPTION OF THE DRAWINGS

FIG. 7 is a flowchart showing a process of generating the variation CT image.

FIG. 8 is a diagram for describing second supervised data including the variation CT image and the correct information as a pair.

DESCRIPTION OF EMBODIMENTS

Figure 1:
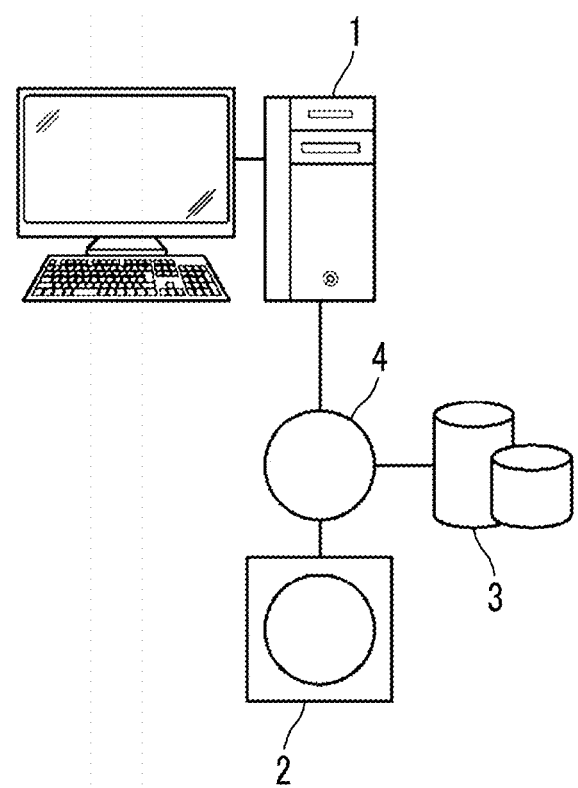
FIG. 1 is a hardware configuration diagram showing an outline of a diagnosis support system to which a learning image generation device and a learning device according to an exemplary embodiment of the present disclosure are applied.

Hereinafter, a first exemplary embodiment of the present disclosure will be described with reference to the drawings. FIG. 1 is a hardware configuration diagram showing an outline of a diagnosis support system to which a learning image generation device and a learning device according to the first exemplary embodiment of the present disclosure are applied. As shown in FIG. 1, in the diagnosis support system, a learning device 1 according to the present exemplary embodiment, a three-dimensional image capturing device 2, and an image storage server 3 are connected via a network 4 in a communicable state. Note that the learning device 1 encompasses a learning model and a learning image generation device according to the present exemplary embodiment.

The three-dimensional image capturing device 2 is an apparatus that images a diagnosis target site of a subject to generate the three-dimensional image showing the site, and a specific example thereof includes a computed tomography (CT) apparatus, a magnetic resonance imaging (MRI) apparatus, and a positron emission tomography (PET) apparatus. A medical image generated by this three-dimensional image capturing device 2 is transmitted to the image storage server 3 and stored therein. Note that in the present exemplary embodiment, the site to be diagnosed of a patient as the subject is a brain, and the three-dimensional image capturing device 2 is the CT device. Moreover, in the CT device, a three-dimensional CT image Bc0 including the brain of the subject is generated.

The image storage server 3 is a computer that stores and manages various data, and comprises a large capacity external storage device and database management software. The image storage server 3 performs communication with other devices via the wired or wireless network 4 to transmit and receive image data. Specifically, the image storage server 3 acquires various data including the image data of the CT image generated by the three-dimensional image capturing device 2 via the network, and stores and manages the data in a recording medium, such as the large capacity external storage device. Note that a storage format of the image data and the communication between the devices via the network 4 are based on a protocol, such as digital imaging and communication in medicine (DICOM). In addition, in the present exemplary embodiment, the image storage server 3 also stores and manages first supervised data D (to be described below) including the CT image Bc0 which is a learning image for learning a learning model 22 to be described below.

The learning device 1 including the learning image generation device according to the present exemplary embodiment and the learning model is a device in which a learning image generation program and a learning program according to the present disclosure are installed in one computer. The computer may be a workstation or a personal computer directly operated by a doctor who makes a diagnosis, or may be a server computer connected to the workstation or the personal computer via the network. The learning image generation program and the learning program are recorded in a recording medium, such as a digital versatile disc (DVD) or a compact disc read only memory (CD-ROM) to be distributed, and are installed in the computer from the recording medium. Alternatively, the learning image generation program and the learning program are stored in a storage device of the server computer connected to the network or a network storage to be accessible from the outside, and are downloaded and installed in the computer used by the doctor in response to a request.

Figure 2:
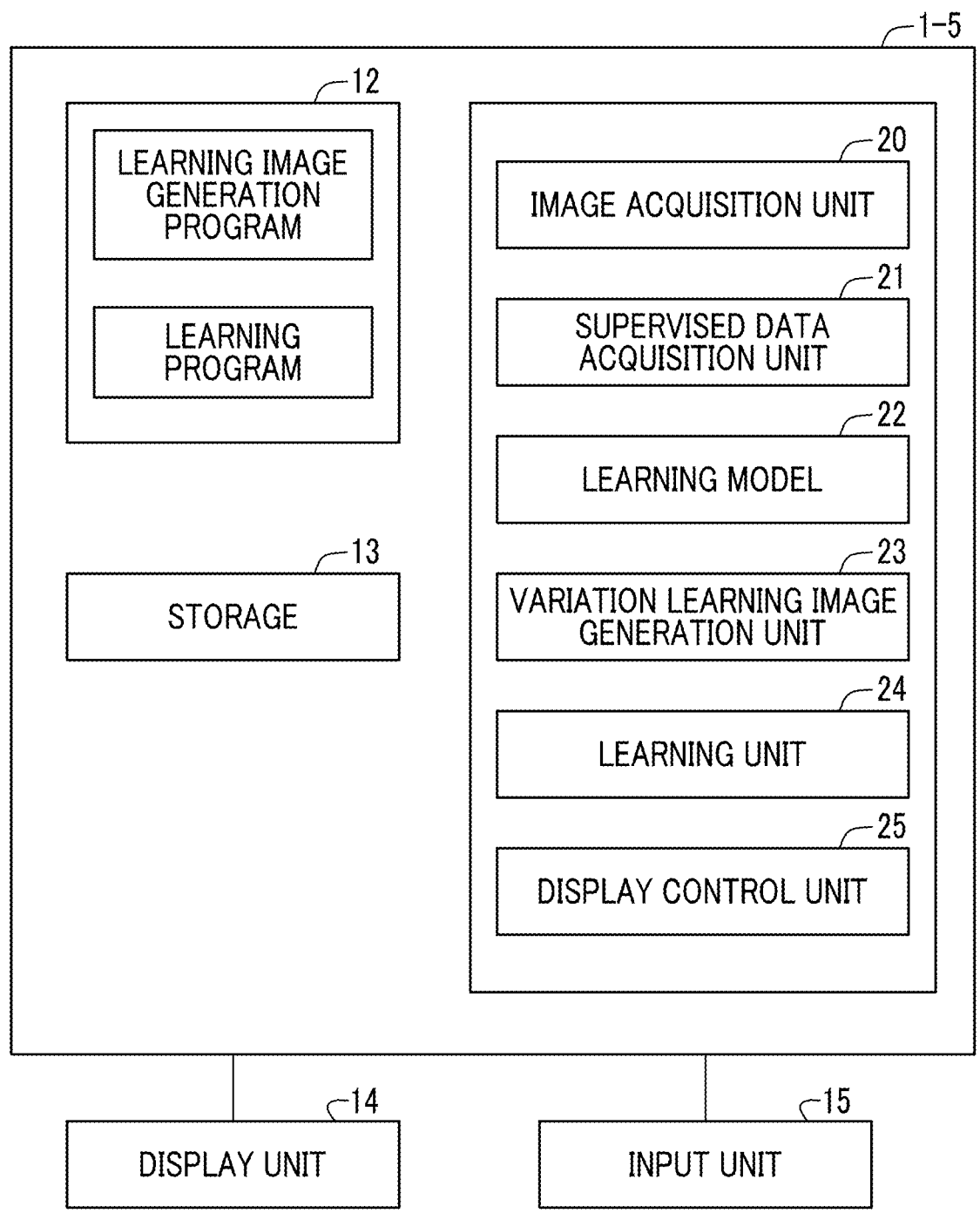
FIG. 2 is a schematic block diagram showing a configuration of the learning device according to a first exemplary embodiment of the present disclosure.

FIG. 2 is a diagram showing a schematic configuration of the learning device 1 which is the exemplary embodiment of the present disclosure realized by installing the learning image generation program and the learning program on the computer. As shown in FIG. 2, the learning device 1 comprises a central processing unit (CPU) 11, a memory 12, and a storage 13, as a configuration of a standard workstation. In addition, the learning device 1 is connected to a display unit 14 including a liquid crystal display and the like and an input unit 15 including a keyboard, a mouse, and the like. The input unit 15 receives various setting inputs by a user. Note that the display unit 14 and the input unit 15 may be used in combination by using a touch panel.

The storage 13 includes a hard disk drive, a solid state drive (SSD), and the like. The storage 13 stores the first supervised data D including the CT image Bc0, which is the learning image for learning the learning model 22 acquired by the image storage server 3 via the network 4, and various pieces of information including information required for the process.

In addition, the learning image generation program and the learning program are stored in the memory 12. The learning image generation program defines an image acquisition process of acquiring the learning image and a variation learning image generation process as processes to be executed by the CPU 11. In the variation learning image generation process, a variation learning image is generated by adding a variation in which an output of the learning model 22 deviates from a target value to a pixel value of at least one pixel that constitutes the learning image in a case in which the acquired learning image is input to the learning model 22.

In addition, the learning program defines, as the processes to be executed by the CPU 11, a supervised data acquisition process of acquiring one or more first supervised data including the learning image and a correct learning image in which a correct region is defined in the learning image as a pair, and one or more second supervised data including one or more variation learning images generated by adding the variation in which the output of the model deviates from the target value to the pixel value of at least one pixel that constitutes the learning image in a case in which the learning image is input to the model, and the correct learning image in which the correct region is defined in the learning image before the variation in each of the one or more variation learning images as a pair, a learning process of learning the model by using the one or more first supervised data and the one or more second supervised data, which are acquired, a discrimination process of output a discrimination result in the input image in a case in which the learning image or a target image to be discriminated input, and a display control process of displaying the learning image, the variation learning image, the discrimination result, and the like on the display unit 14.

Moreover, by the CPU 11 executing these processes in response to the program, the computer functions as an image acquisition unit 20, a supervised data acquisition unit 21, the learning model 22, a variation learning image generation unit 23, a learning unit 24, and a display control unit 25. Here, the image acquisition unit 20 and the variation learning image generation unit 23 configure the learning image generation device according to the present exemplary embodiment.

The display control unit 25 displays the CT image Bc0 acquired by the image acquisition unit 20, a variation CT image Bc2 described below, the discrimination result, and the like on the display unit 14.

Figure 3:
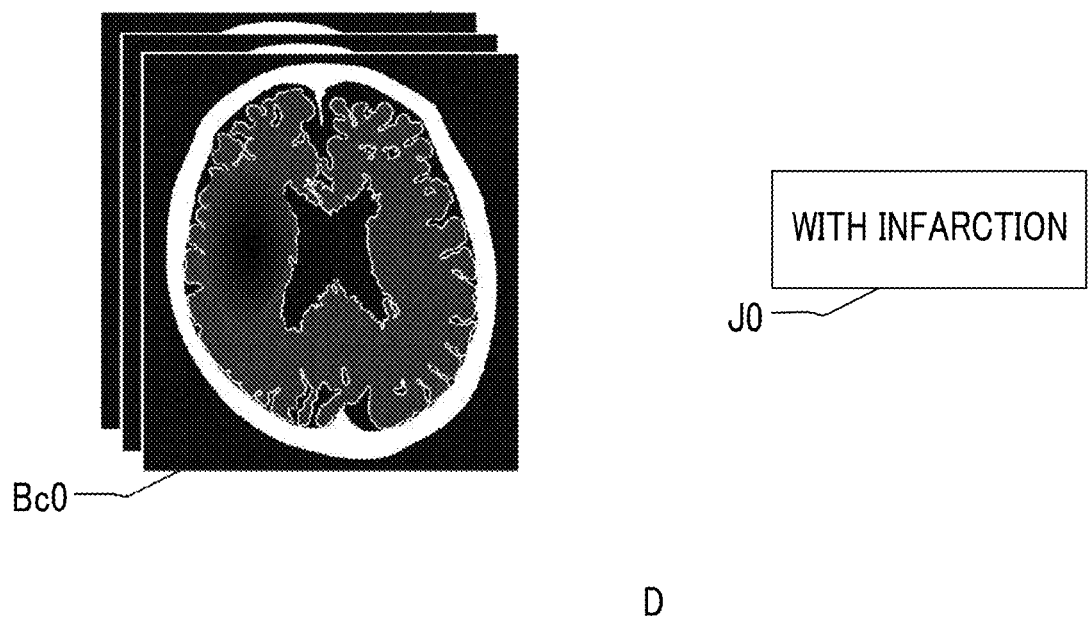
FIG. 3 is a diagram for describing first supervised data D including a CT image and correct information as a pair.

The image acquisition unit 20 acquires the CT image Bc0 from the image storage server 3 via an interface (not shown) connected to the network. FIG. 3 is a diagram for describing the first supervised data D including the CT image Bc0 and correct information JO as a pair. The CT image Bc0 shown in FIG. 3 is the learning image for learning the learning model 22 described below. Note that in FIG. 3, although the CT image Bc0 is the three-dimensional image, here, for the sake of description, the description will be made by using a two-dimensional tomographic image on one tomographic plane of the CT image Bc0. Note that in a case in which the CT image Bc0 is already stored in the storage 13, the image acquisition unit 20 may acquire the CT image Bc0 from the storage 13. In addition, the image acquisition unit 20 acquires the CT images Bc0 for a large number of subjects for learning the learning model 22 to be described below.

The supervised data acquisition unit 21 acquires the first supervised data D from the image storage server 3 via an interface (not shown) connected to the network. As shown in FIG. 3, the first supervised data D is data including the CT image Bc0 and the information indicating "with the infarction" or "without the infarction" as the correct information JO in the CT image Bc0 as a pair. Note that the correct information JO of "with the infarction" or "without the infarction" may be manually input by the user from the input unit 15. In addition, in a case in which the CT image Bc0 is input to the learning model 22, in a case in which the discrimination result based on a value of an output value S(x) of the learning model 22 with respect to a whole x of the CT image Bc0 is "with the infarcted region" (see Table 1), the CT image Bc0 may be the image "with the infarction".

Figure 4:
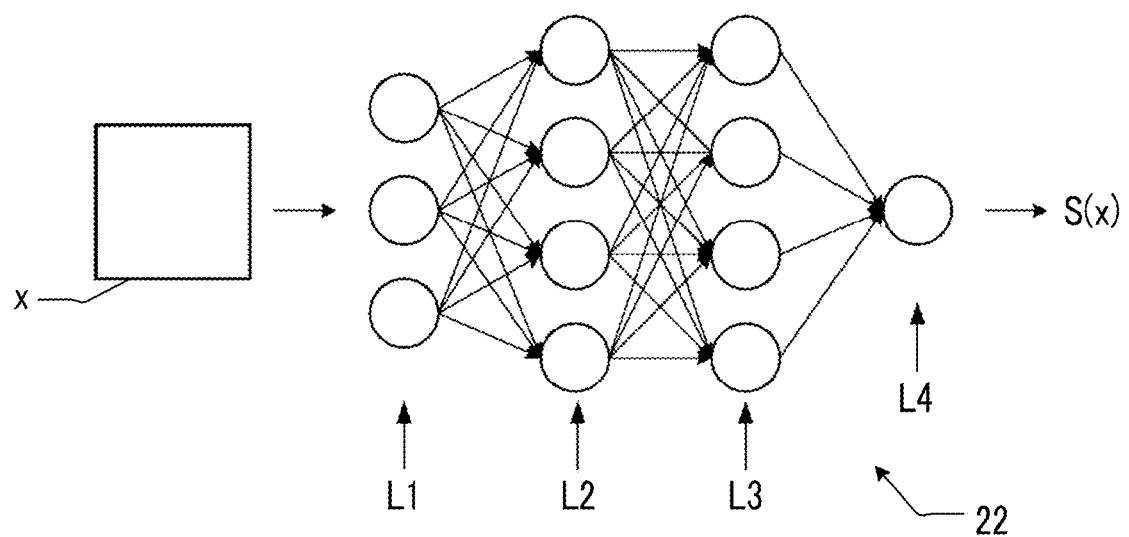
FIG. 4 is a diagram showing an example of a learning model.

The learning model 22 discriminates the presence or absence of a diseased region in the CT image Bc0. That is, it is the model for discriminating the classification of CT image Bc0 (whether or not there is the diseased region). In the present exemplary embodiment, the diseased region is defined as the infarcted region as an example. In the present exemplary embodiment, the learning model 22 is the model in which a plurality of processing layers are hierarchically connected and deep learning is performed. FIG. 4 is a diagram showing an example of the learning model 22. Note that the learning model 22 corresponds to a model of the present disclosure.

As shown in FIG. 4, the learning model 22 includes an input unit L1 including three input layers, a first processing unit L2 including four processing layers, a second processing unit L3 including four processing layers, and an output unit L4 including one output layer. The input layers, the processing layers, and the output layer are connected as shown in FIG. 4.

In the present exemplary embodiment, the first processing unit L2 and the second processing unit L3 are learned to output the output value S(x) indicating the discrimination result of whether or not there is the infarcted region in the whole x of the input CT image Bc0 by using, as the supervised data, the data set including a number of the CT images Bc0 of the brain including the infarcted region and the correct information that is the discrimination result in the CT image Bc0. Note that the correct information is the information on whether or not there is the infarcted region in the whole x of the CT image Bc0.

As a result, in a case in which the CT image Bc0 is input to the input layer of the first processing unit L2, a feature amount map output from the processing layer on the previous stage in the plurality of processing layers of the first processing unit L2 and the second processing unit L3 is sequentially input to the processing layer of the next stage. Next, the output value S(x) indicating the discrimination result of whether or not there is the infarcted region in the whole x of the CT image Bc0 is output from the output layer of the output unit L4. Note that the output value S(x) output by the output unit L4 is a value indicating the discrimination result of whether or not there is the infarcted region in the whole x of the CT image Bc0. Here, Table 1 below shows examples of the output value S(x) and the discrimination result by the learning model 22.

TABLE 1

| Output value S(x) | Discrimination result |
|---|---|
| 0 ≤ S(x) < 0.5 | Without infarcted region |
| 0.5 ≤ S(x) ≤ 1 | With infarcted region |

In a case in which the output value S(x) of the learning model 22 is 0 or more and less than 0.5, it is discriminated that there is no infarcted region, and in a case in which the output value S(x) of the learning model 22 is 0.5 or more and 1 or less, it is discriminated that there is the infarction. That is, for example, in a case in which the CT image Bc0 is input to the learning model 22, in a case in which the output value S(x) of the learning model 22 is 0.6, there is the infarcted region in the CT image Bc0. In addition, in a case in which the CT image Bc0 is input to the learning model 22, in a case in which the output value S(x) of the learning model 22 is 0.3, there is no infarcted region in the CT image Bc0.

The variation learning image generation unit 23 generates the variation CT image Bc2 by adding the variation in which the output of the learning model 22 deviates from the target value to the pixel value of at least one pixel that constitutes the CT image Bc0 in a case in which the CT image Bc0 is input to the learning model 22. For example, for the CT image Bc0 before the variation, in a case in which the output value S(x) of the learning model 22 is 0.6, it is discriminated that there is the infarcted region in the CT image Bc0. Since this CT image Bc0 is the image with the infarcted region, "1", which is the output value S(x) discriminated to have the highest possibility of having the infarcted region, is the "target value". Therefore, the "variation deviating from the target value" is the variation added to the pixel value having a value at which the output value S(x) of the learning model 22 further deviates from "1" (less than "1"), the value being 0.5 or more and less than 0.6. On the other hand, for the CT image Bc0 before the variation, in a case in which the output value S(x) of the learning model 22 is 0.3, the CT image Bc0 is the image without the infarcted region. Since this CT image Bc0 is the image without the infarction, "0", which is the output value S(x) discriminated to have the highest possibility of having no infarcted region, is the "target value". Therefore, the "variation deviating from the target value" is the variation added to the pixel value having a value at which the output value S(x) of the learning model 22 further deviates from "0", the value being more than 0.3 and less than 0.5.

Specifically, the variation learning image generation unit 23 acquires a gradient M(x) of the output value S(x) of the learning model 22 with respect to the whole x of the CT image Bc0 in a case in which the CT image Bc0 is first input to the learning model 22. The gradient M(x) of the output value S(x) of the learning model 22 with respect to the whole x of the CT image Bc0 is derived by Expression (1).

$$M(x) = \partial S(x)/\partial x \qquad (1)$$

Figure 5:
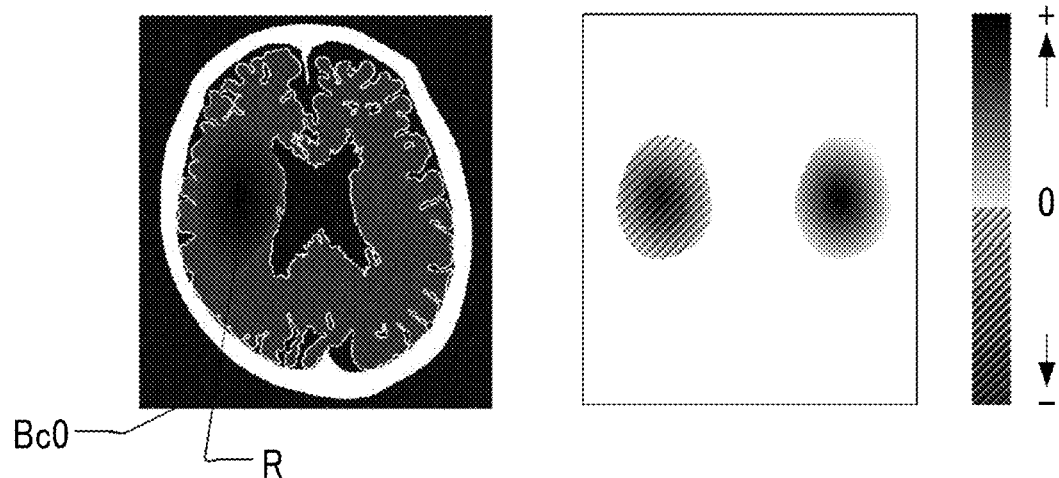
FIG. 5 is a diagram for describing a gradient.

FIG. 5 is a diagram for describing the gradient M(x). The left figure of FIG. 5 is an example of the CT image Bc0, and the right figure is a diagram in which the value of the gradient M(x) in the CT image Bc0 shown in the left figure is plotted. Note that in the left figure of FIG. 5, there is a black region on the left side of the image as compared with the right side. This black region indicates an opinion of cerebral infarction R. As shown in the right figure of FIG. 5, the gradient M(x) on the region on the left side indicated by the diagonal line, that is, the region side having the opinion of the cerebral infarction R is a negative value, and the gradient M(x) on the region on the right side indicated by color other than the diagonal line, that is, the region side having no opinion of the cerebral infarction is a positive value. In addition, as the color is darker, an absolute value of the gradient M(x) is larger.

For the pixel belonging to the region on the left side shown in the right figure of FIG. 5 indicated by the diagonal line, that is, the pixel belonging to the region having the opinion of the cerebral infarction R, the output value S(x) of the learning model 22 is increased as the pixel value is decreased. That is, as the pixel value in the region on the left side indicated by the diagonal line is decreased, the density of the black of the region increased and the output is increased. That is, it is more like a case of the cerebral infarction.

On the other hand, for the pixel belonging to the region on the right side shown in the right figure of FIG. 5 indicated by color other than the diagonal line, the output value S(x) of the learning model 22 is increased as the pixel value is increased. That is, in the region on the right side indicated by color other than the diagonal line, the region is more white as the pixel value is increased, and the density of the black of the region side having the opinion of the cerebral infarction R is relatively increased in a case in which the right and left sides are compared, so that the output is increased. That is, it is more like a case of the cerebral infarction.

In this way, by using the gradient M(x), it is possible to easily derive a variation aspect of the output value S(x) of the learning model 22 depending on the variation of the pixel value.

Next, by using the gradient M(x) derived from Expression (1), the variation CT image Bc2 is generated by adding the variation to the pixel value of the pixel that constitutes the CT image Bc0 in accordance with Expression (2).

$$xa = x - k \times M(x) \quad (2)$$

Note that a fixed number is k>0.

Here, xa indicates the whole variation CT image Bc2 after the whole x of the CT image Bc0 is varied. In addition, k×M(x) represents the whole gradient image shown in the right figure of FIG. 5.

Figure 6:
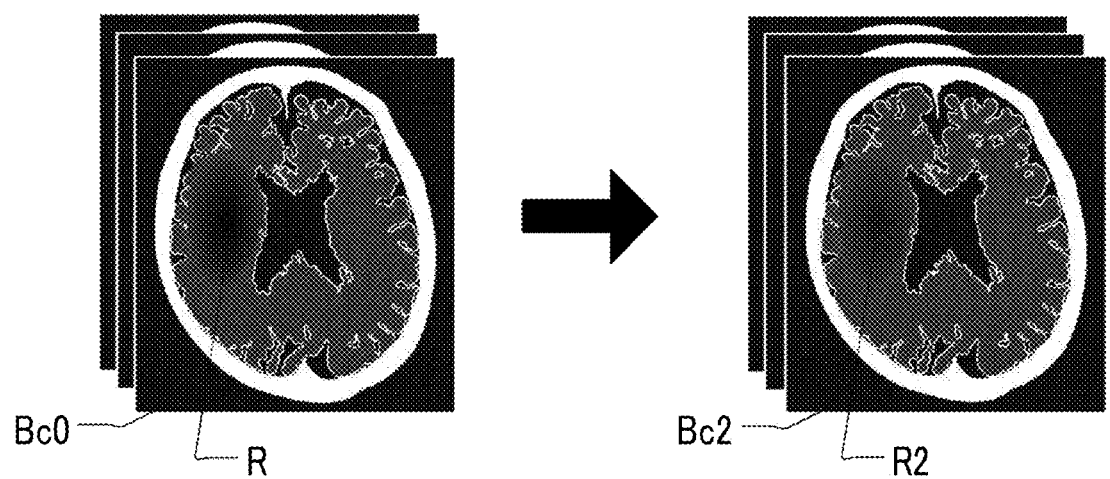
FIG. 6 is a diagram for describing a variation CT image generated by adding the variation to the CT image.

The variation learning image generation unit 23 adds the variation to the pixel value of the pixel that constitutes the CT image Bc0 by subtracting the whole gradient image k×M(x) shown in the right figure of FIG. 5 from the whole x of the CT image Bc0 shown in the left figure of FIG. 5. FIG. 6 is a diagram for describing the variation CT image Bc2 generated by adding the variation to the CT image Bc0.

In a case in which the variation learning image generation unit 23 subtracts the whole gradient image k×M(x) from the whole x of the CT image Bc0, as shown in FIG. 6, in the region in the CT image Bc0 having the opinion of the cerebral infarction R, the pixel value is added and the output is decreased. Therefore, in the variation CT image Bc2, the black color of the region R2 corresponding to the cerebral infarction R is weakened, which makes it less likely to be a case of the cerebral infarction. In addition, in the region in the CT image Bc0 on the side opposite to the side having the opinion of the cerebral infarction R, the pixel value is reduced and the output is increased. Therefore, in the variation CT image Bc2, the density of the black of the region corresponding to the side opposite to the cerebral infarction R is increased, which makes it less likely to be a case of the cerebral infarction.

In this way, by adding the variation deviating from the "target value" to the whole x of the CT image Bc0, it is possible to generate the variation CT image Bc2, which is difficult for the learning model 22 to correctly recognize the infarcted region as compared with the CT image Bc0 before the variation.

Next, a process of generating the variation CT image Bc2 according to the present exemplary embodiment will be described. FIG. 7 is a flowchart showing the process of generating the variation CT image Bc2. First, the image acquisition unit 20 acquires the CT image Bc0 (step ST1). Next, the variation learning image generation unit 23 acquires the gradient M(x) of the output value S(x) of the learning model 22 with respect to the whole x of the CT image Bc0 in a case in which the CT image Bc0 is input to the learning model 22 (step ST2). Moreover, as described above, the variation learning image generation unit 23 generates the variation CT image Bc2 by adding the variation deviating from the "target value" to the whole x of the CT image Bc0 (step ST3), and terminates a series of processes.

With the learning image generation device of the present exemplary embodiment, which is configured by the image acquisition unit 20 and the variation learning image generation unit 23, the learning image generation method of the present exemplary embodiment, and the learning image generation program of the present exemplary embodiment, by adding the variation deviating from the "target value" to the whole x of the CT image Bc0, it is possible to generate the variation CT image Bc2, which is difficult for the learning model 22 to correctly recognize the infarcted region as compared with the CT image Bc0 before the variation. In addition, by changing a value of k in Expression (2), it is possible to generate a plurality of the variation CT images Bc2 having different pixel values of the pixels that constitute the CT image Bc0. As a result, the variation CT image Bc2, which is the CT image other than the limited CT image Bc0, can also be used as the learning image. Therefore, by using the limited CT image Bc0, the learning model 22 can be learned to be stably operated for an unknown CT image other than the CT image Bc0.

Note that as the value of k in Expression (2), a certain value, which is set in advance, may be used, or the value may be randomly changed and used. In addition, as will be described below, in a case in which the learning model 22 is learned, the value may be changed depending on the progress of the learning. In addition, an upper limit value may be provided for the value of k in Expression (2). As a result, it is possible to prevent the variation CT image Bc2 from becoming an abnormal image. In this case, the upper limit value can be set depending on, for example, an allowable value of the pixel value.

The variation CT image Bc2 generated by the variation learning image generation unit 23 as described above is stored in the storage 13 as the image data constituting the second supervised data F. FIG. 8 is a diagram for describing the second supervised data F including the variation CT image Bc2 and correct information J2 as a pair. As shown in FIG. 8, the second supervised data F is data including the variation CT image Bc2 and the information indicating "with the infarction" or "without the infarction" as the correct information J2 in the CT image Bc0 before the variation as a pair. Note that the correct information J2 of "with the infarction" or "without the infarction" may be manually input by the user from the input unit 15. In addition, in a case in which the CT image Bc0 before the variation is input to the learning model 22, in a case in which the discrimination result based on the value of output value S(x) of the learning model 22 with respect to a whole x of the CT image Bc0 before the variation is "with the infarcted region", the CT image Bc0 and the variation CT image Bc2, which is varied, may be the image "with the infarction".

Figure 9:
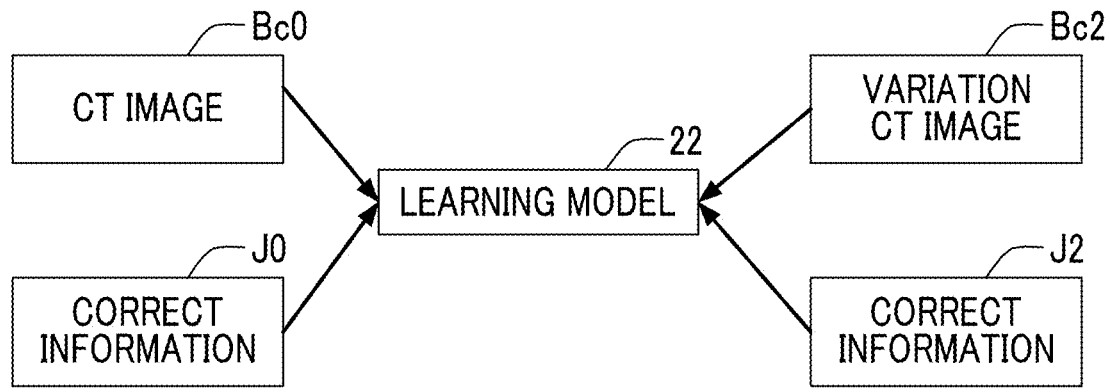
FIG. 9 is a diagram for describing the learning model.

Next, returning to FIG. 2, the learning unit 24 learns the learning model 22 by using one or more first supervised data D and one or more second supervised data F, which are acquired by the supervised data acquisition unit 21. FIG. 9 is a diagram for describing a learning method of the learning model. Note that in the present exemplary embodiment, the learning model 22 corresponds to the model according to the present disclosure.

As shown in FIG. 9, the learning unit 24 inputs the first supervised data D, that is, the CT image Bc0 and the correct information J0 to a learning model 22 to cause the learning model 22 to learn the presence or absence of the infarcted region in the CT image Bc0. As a result, in a case in which the CT image Bc0 is input, the learning model 22 is learned to output the presence or absence of the infarcted region in the CT image Bc0. In addition, the learning unit 24 inputs the second supervised data F, that is, the variation CT image Bc2 and the correct information J2 to a learning model 22 to cause the learning model 22 to learn the presence or absence of the infarcted region in the variation CT image Bc2. As a result, in a case in which the variation CT image Bc2 is input, the learning model 22 is learned to output the presence or absence of the infarcted region in the variation CT image Bc2.

Next, the learning method of the learning model 22 by using the one or more first supervised data D and the one or more second supervised data F will be described. Generally, in a case in which the learning model 22 is learned, for example, n supervised data are learned by the learning model 22 in order. Moreover, in a case in which all of the n supervised data are learned, the learning model 22 is learned by using the n supervised data again as second learning, and the learning model 22 is learned by using the same supervised data a predetermined number of times.

Figure 10:
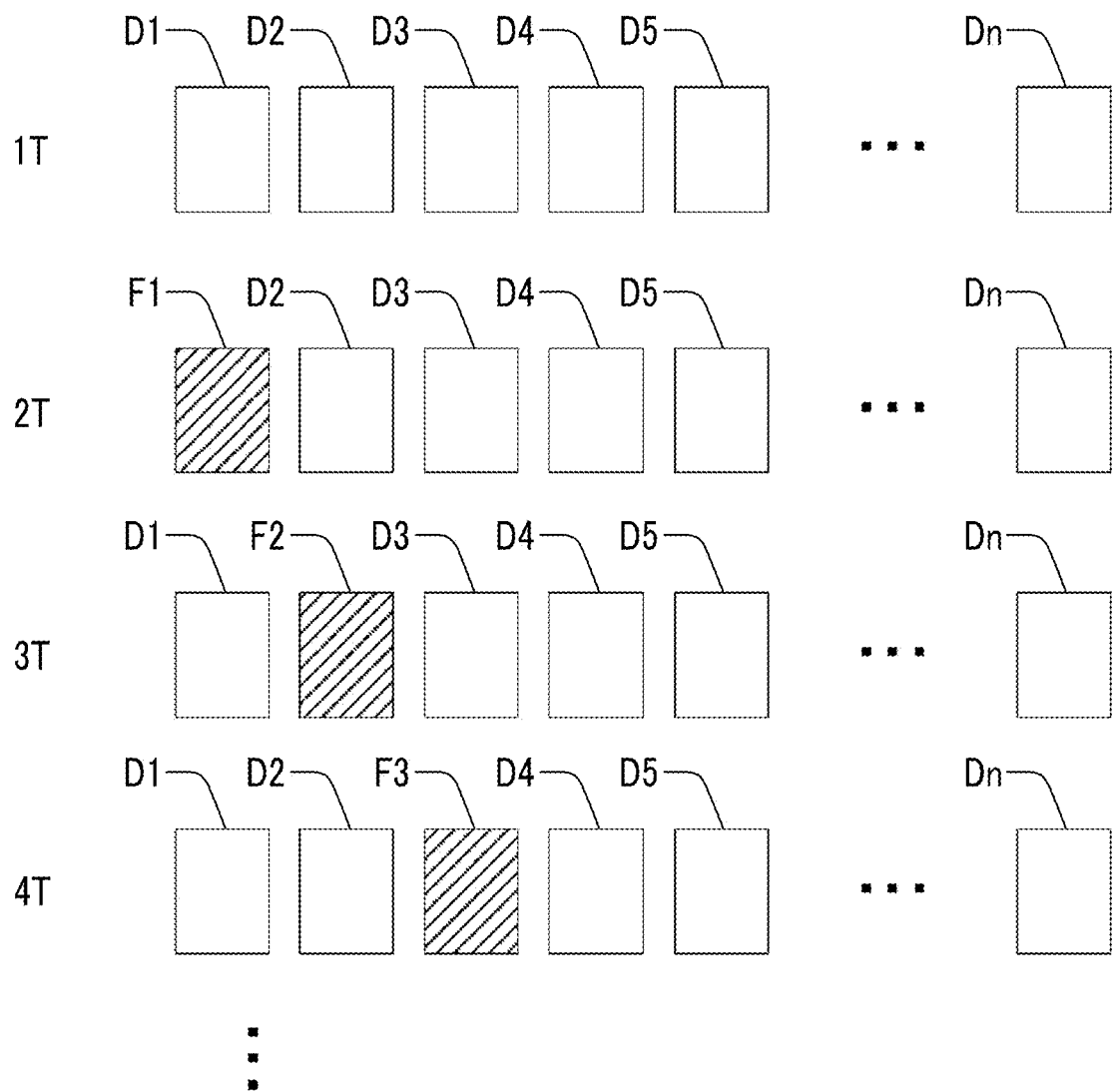
FIG. 10 is a diagram for describing a learning method using the first supervised data and the second supervised data according to a second exemplary embodiment.

In the present exemplary embodiment, in a case in which the learning model 22 is learned by using n first supervised data D1 to Dn, the learning model 22 is first learned by using n first supervised data D1 to Dn in first learning, and at least one first supervised data D of the n first supervised data D1 to Dn is replaced with the second supervised data F to learn the learning model 22 in the second and subsequent learning. FIG. 10 is a diagram for describing the learning method using the first supervised data D and the second supervised data F in a second exemplary embodiment. Note that the first supervised data D and the second supervised data F are a combination of the CT image Bc0 or the variation CT image Bc2 and the correct information J0 or the correct information J2, that is, are constituted by two data, but in FIG. 10, the first supervised data D and the second supervised data F are represented by one image for convenience of description. Note that it may be represented in the same manner in the following drawings.

As shown in FIG. 10, the learning unit 24 learns the learning model 22 by using the n first supervised data D1 to Dn at the time of the first learning (1T). At the time of second learning (2T), the learning model 22 is learned by replacing the first supervised data D1 with second supervised data F1. At the time of third learning (3T), the second supervised data F1 is returned to the first supervised data D1, and the first supervised data D2 is replaced with second supervised data F2 to learn the learning model 22. Further, at the time of fourth learning (4T), the second supervised data F2 is returned to the first supervised data D2, and the first supervised data D3 is replaced with second supervised data F3 to learn the learning model 22.

As described above, in the second exemplary embodiment, in the second and subsequent learning, the learning model 22 is learned by replacing one first supervised data D of the n first supervised data D1 to Dn with the second supervised data F for each learning. In a case in which n+1 learning is terminated, the process returns to the first learning (1T), and the learning described above is repeated until the set number of learning is terminated.

Figure 11:
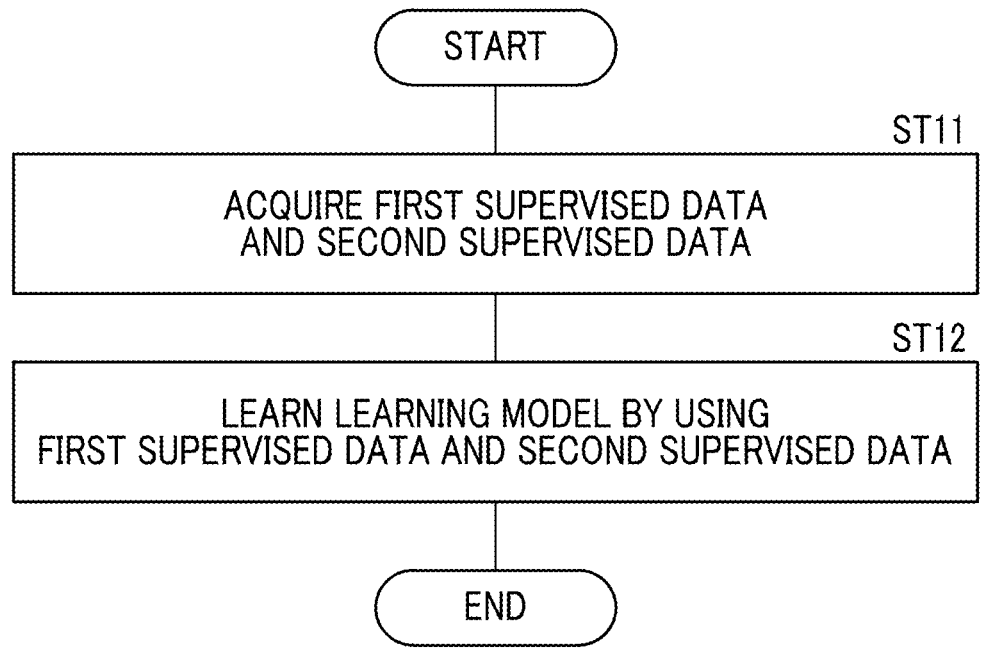
FIG. 11 is a flowchart showing a process performed at the time of learning.

Then, a series of processes in the second exemplary embodiment will be described. FIG. 11 is a flowchart showing a process performed at the time of learning. First, the supervised data acquisition unit 21 acquires the first supervised data D and the second supervised data F from the image storage server 3 and the storage 13 (step ST11). Next, the learning unit 24 learns the learning model 22 as described above by using the first supervised data D and the second supervised data F, which are acquired (step ST12), and terminates a series of processes.

In the second exemplary embodiment, the second supervised data F including the variation CT image Bc2 and the correct information J2 as a pair generated by adding the variation in which the output of the model deviates from the "target value" for the whole x of the CT image Bc0 to the pixel that constitutes the CT image Bc0 is used for learning. In this way, by using the second supervised data F rather than learning the learning model 22 by using only the first supervised data D, the variation CT image Bc2 which is the CT image other than the limited CT image Bc0 can also be used as the learning image. That is, by using the limited CT image Bc0, the learning model 22 can be learned to be stably operated even for the unknown CT image other than the CT image Bc0.

Figure 12:
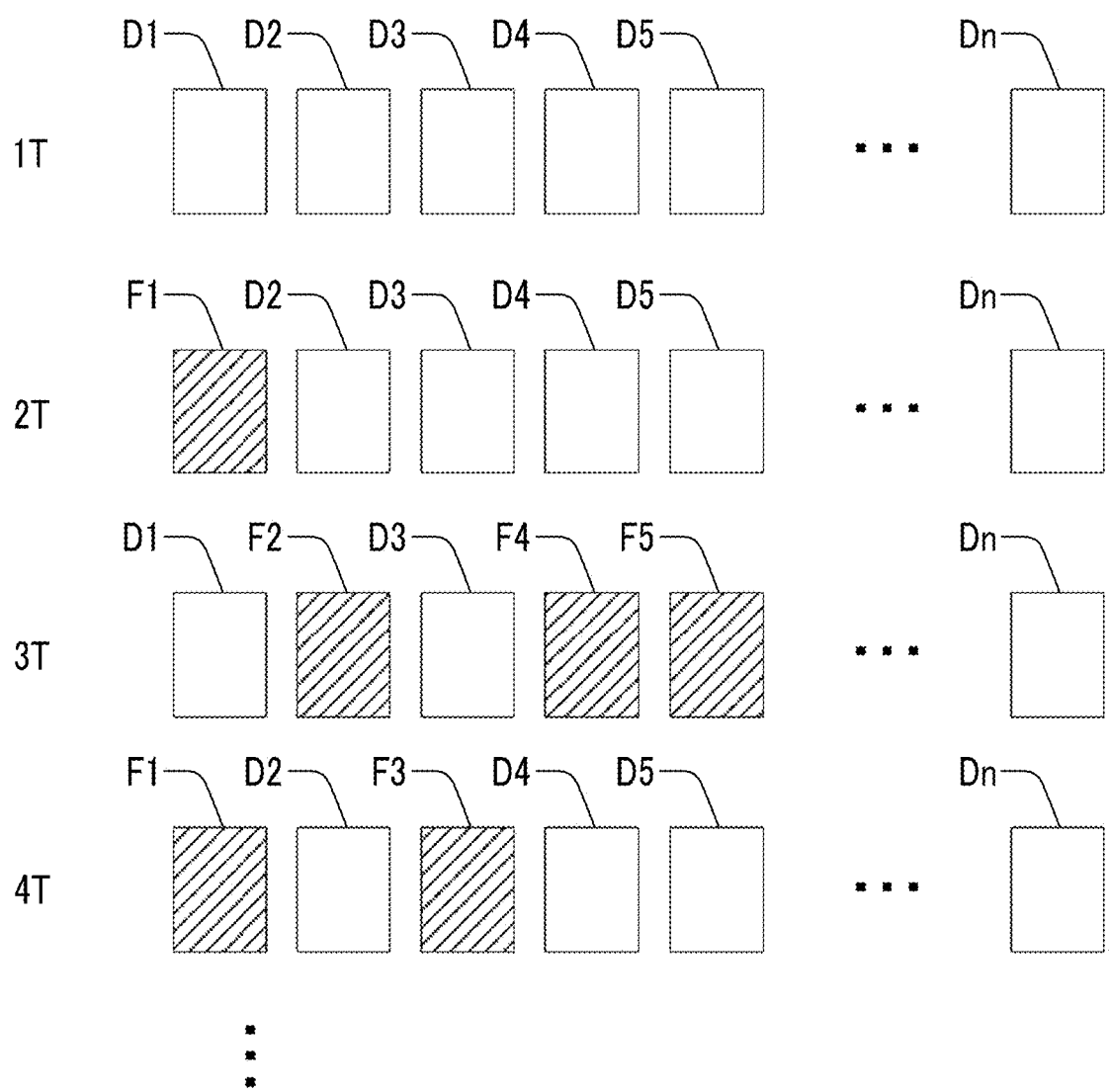
FIG. 12 is a diagram for describing the learning method using the first supervised data and the second supervised data according to a third exemplary embodiment.

Note that in the second exemplary embodiment, in the second and subsequent learning, one first supervised data D is replaced with the second supervised data F to learn the learning model 22 for each learning, but the technology of the present disclosure is not limited to this. The two first supervised data D may be replaced with the second supervised data F, or any number of the first supervised data D, such as three or four, can be replaced with the second supervised data F. In addition, only a predetermined first supervised data D may be replaced with the second supervised data F which is different for each learning. In addition, the first supervised data D to be changed to the second supervised data F may be randomly selected. In addition, the number of the first supervised data D to be changed to the second supervised data F may be randomly determined. In addition, both the first supervised data D to be changed to the second supervised data F and the number of the first supervised data D to be changed to the second supervised data F may be randomly determined. FIG. 12 is a diagram for describing the learning method using the first supervised data D and the second supervised data F in a third exemplary embodiment.

As shown in FIG. 12, the learning unit 24 learns the learning model 22 by using the n first supervised data D1 to Dn at the time of the first learning (1T). At the time of second learning (2T), the learning model 22 is learned by replacing the first supervised data D1 with second supervised data F1. At the time of the third learning (3T), the learning model 22 is learned by returning the second supervised data F1 to the first supervised data D1 and by replacing the first supervised data D2 with the second supervised data F2, the first supervised data D4 with second supervised data F4, and the first supervised data D5 with second supervised data F5. Further, at the time of the fourth learning (4T), the learning model 22 is learned by returning the second supervised data F2 to the first supervised data D2, the second supervised data F4 to first supervised data D4, and the second supervised data F5 to the first supervised data D5, and by replacing the first supervised data D1 with the second supervised data F1 and the first supervised data D3 with the second supervised data F3.

Figure 13:
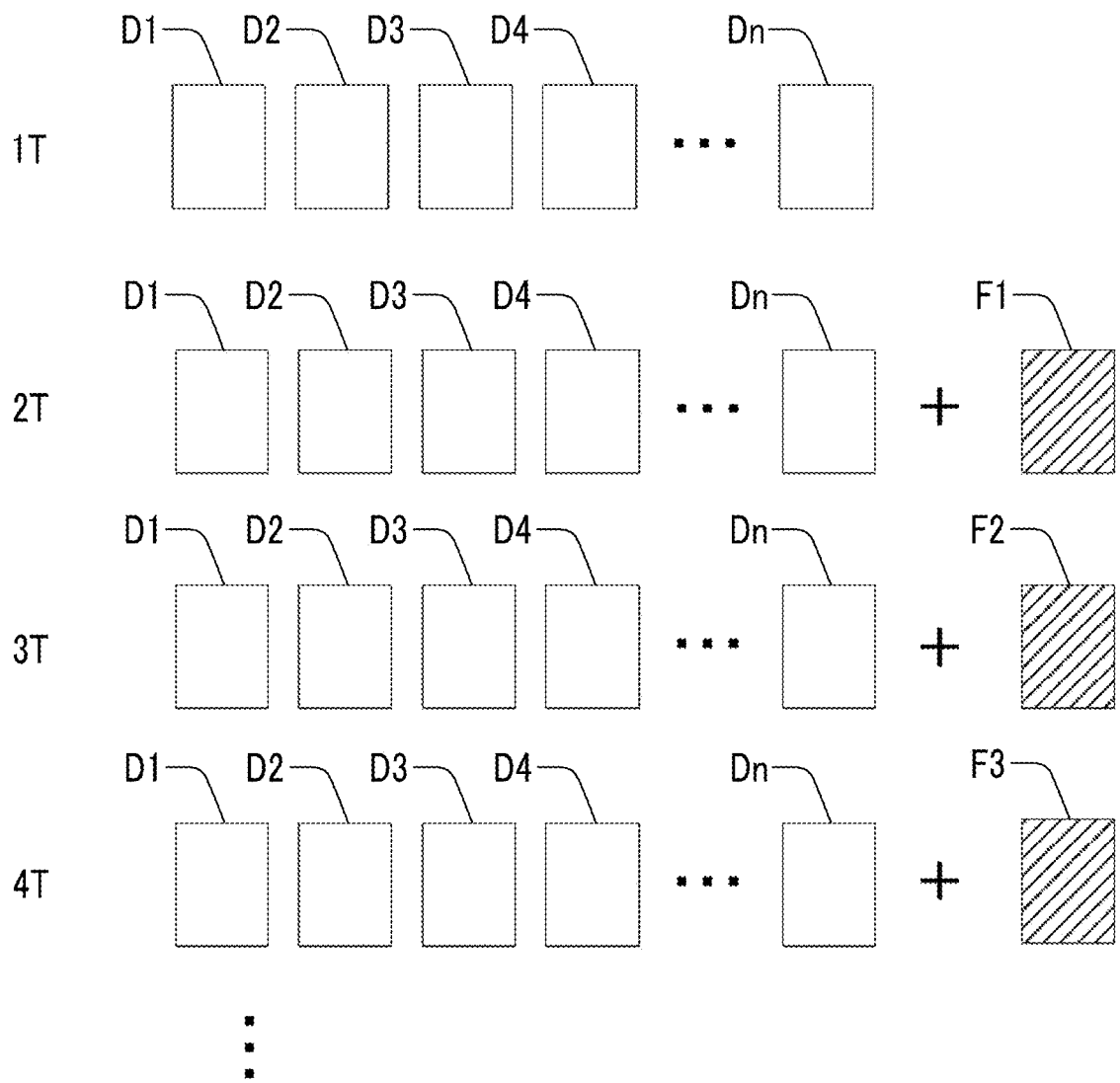
FIG. 13 is a diagram for describing the learning method using the first supervised data and the second supervised data according to a fourth exemplary embodiment.

Note that in the second exemplary embodiment and the third exemplary embodiment, in the second and subsequent learning, the first supervised data D is replaced with the second supervised data F to learn the learning model 22 for each learning, but the technology of the present disclosure is not limited to this. The learning model 22 may be learned by adding the second supervised data F to the n first supervised data Dn for each learning. FIG. 13 is a diagram for describing the learning method using the first supervised data D and the second supervised data F in a fourth exemplary embodiment.

As shown in FIG. 13, the learning unit 24 learns the learning model 22 by using the n first supervised data D1 to Dn at the time of the first learning (1T). At the time of the second learning (2T), the learning model 22 is learned by adding the second supervised data F1. At the time of the third learning (3T), the learning model 22 is learned by adding the second supervised data F2. Further, at the time of the fourth learning (4T), the learning model 22 is learned by adding the second supervised data F3.

As described above, in the fourth exemplary embodiment, in the second and subsequent learning, the learning model 22 is learned by further adding one second supervised data F to the n first supervised data D1 to Dn for each learning. In a case in which n+1 learning is terminated, the process returns to the first learning (1T), and the learning described above is repeated until the set number of learning is terminated.

Figure 14:
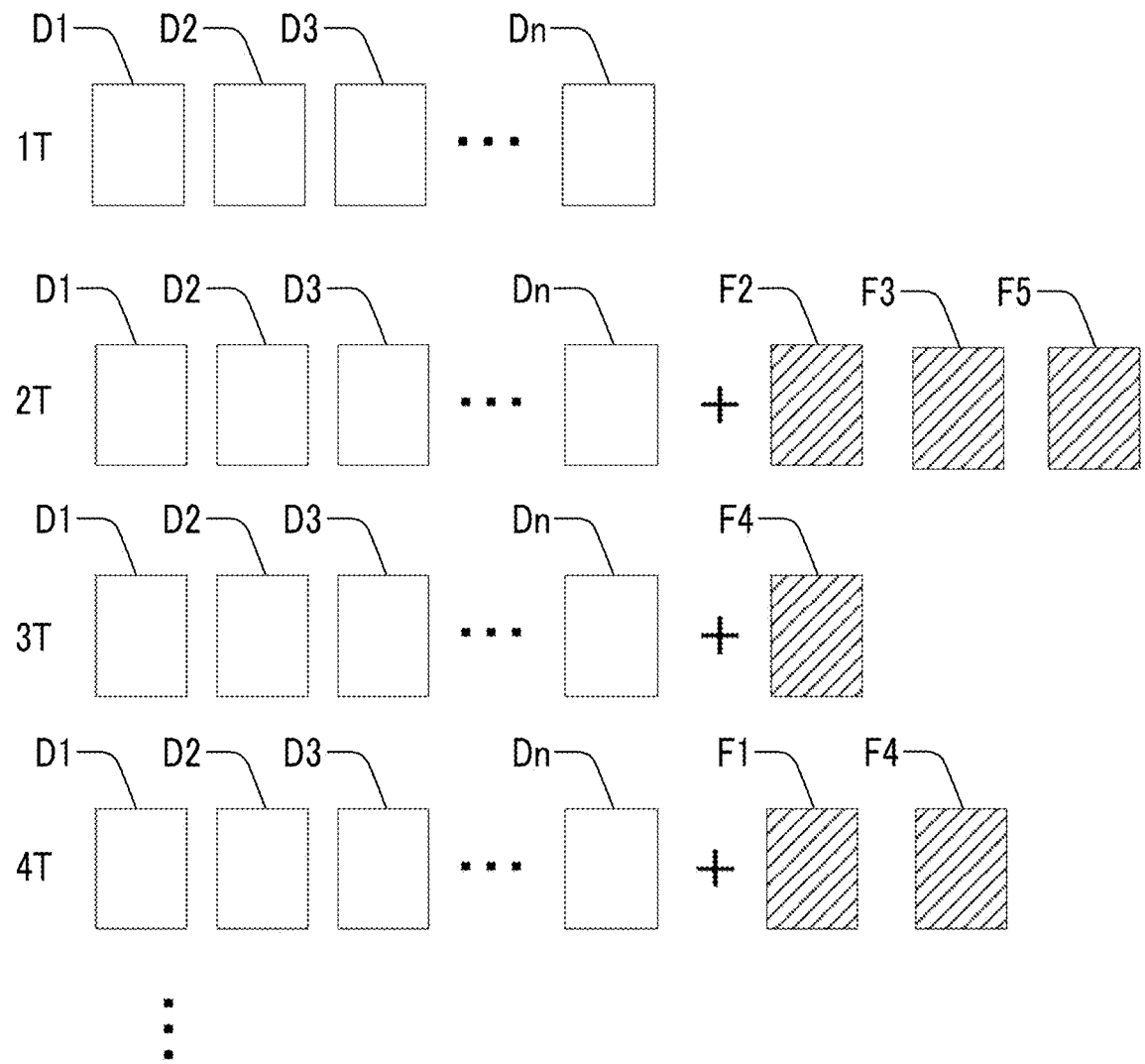
FIG. 14 is a diagram for describing the learning method using the first supervised data and the second supervised data according to a fifth exemplary embodiment.

Note that in the fourth exemplary embodiment, in the second and subsequent learning, one second supervised data F is added to learn the learning model 22 for each learning, but the technology of the present disclosure is not limited to this. Two second supervised data F may be added, or any number of the second supervised data F, such as three or four, can be added. In addition, the second supervised data F to be added may be randomly selected. FIG. 14 is a diagram for describing the learning method using the first supervised data D and the second supervised data F in a fifth exemplary embodiment.

As shown in FIG. 14, the learning unit 24 learns the learning model 22 by using the n first supervised data D1 to Dn at the time of the first learning (1T). At the time of the second learning (2T), the learning model 22 is learned by adding the second supervised data F2, the second supervised data F3, and the second supervised data F5. At the time of the third learning (3T), the learning model 22 is learned by adding the second supervised data F4. Further, at the time of the fourth learning (4T), the learning model 22 is learned by adding the second supervised data F1 and the second supervised data F4.

As described above, in the fifth exemplary embodiment, in the second and subsequent learning, the learning model 22 is learned by adding a random number of the second supervised data F to the n first supervised data D1 to Dn for each learning until the set number of learning is terminated.

Figure 15:
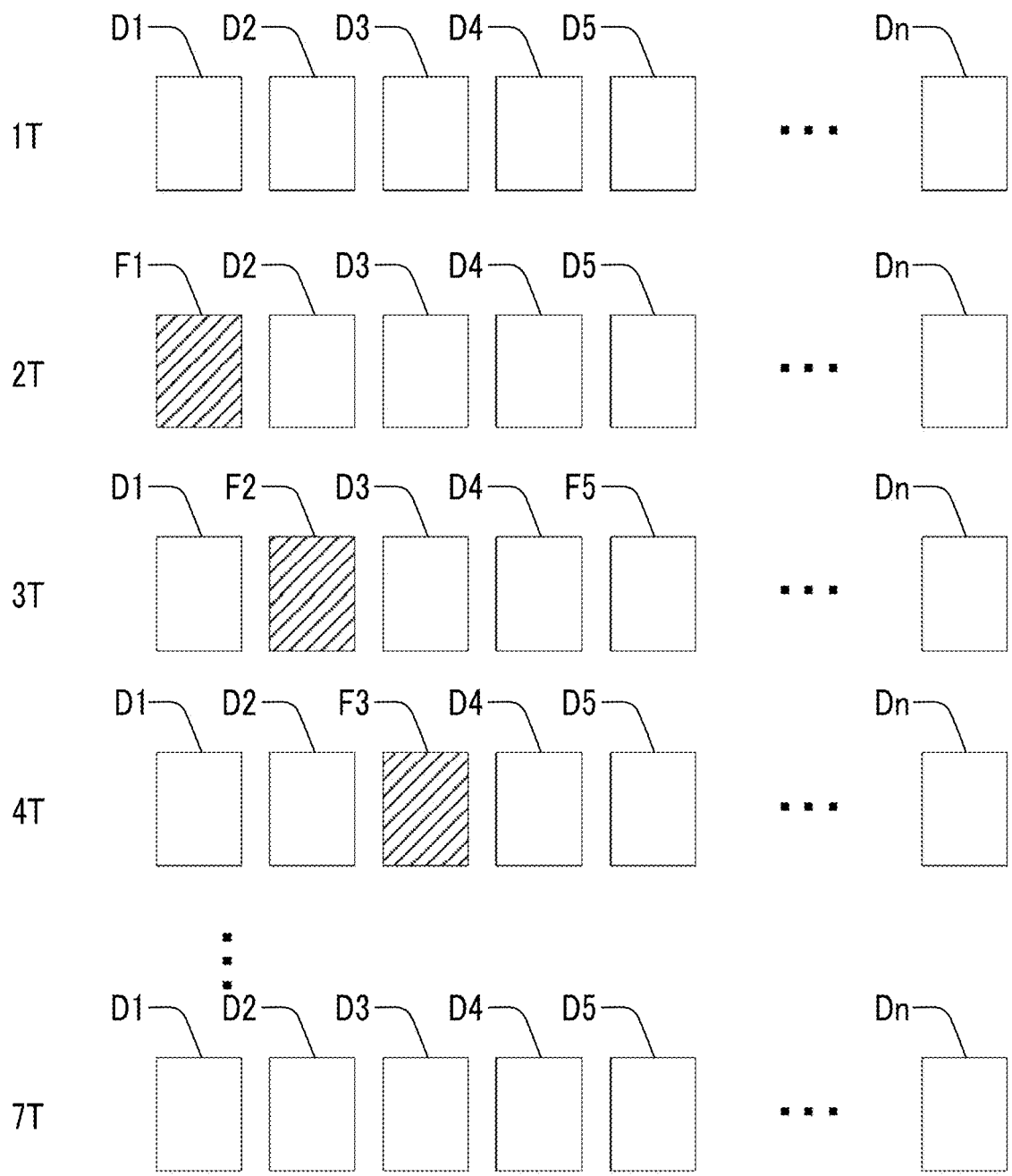
FIG. 15 is a diagram for describing the learning method using the first supervised data and the second supervised data according to a sixth exemplary embodiment.

Note that the learning method of the learning model 22 according to the present disclosure is not limited to the learning method shown in the second to fifth exemplary embodiments. FIG. 15 is a diagram for describing the learning method using the first supervised data D and the second supervised data F in a sixth exemplary embodiment.

As shown in FIG. 15, the learning unit 24 learns the learning model 22 by using only the n first supervised data D1 to Dn in the second and subsequent learning at least once, and in the seventh learning in the present exemplary embodiment. Note that the number of learning of the learning model 22 by using only the n first supervised data D1 to Dn is not limited to the seventh learning, and may be any learning. In addition, the learning model 22 may be learned by using only the n first supervised data D1 to Dn twice, three times, and n times.

Note that in the exemplary embodiments described above, the second supervised data F may use the variation CT image Bc2 in which the value of k in Expression (2) is changed and varied for each learning. In this case, the value of k may be randomly changed for each learning, or may be a predetermined value.

Figure 16:
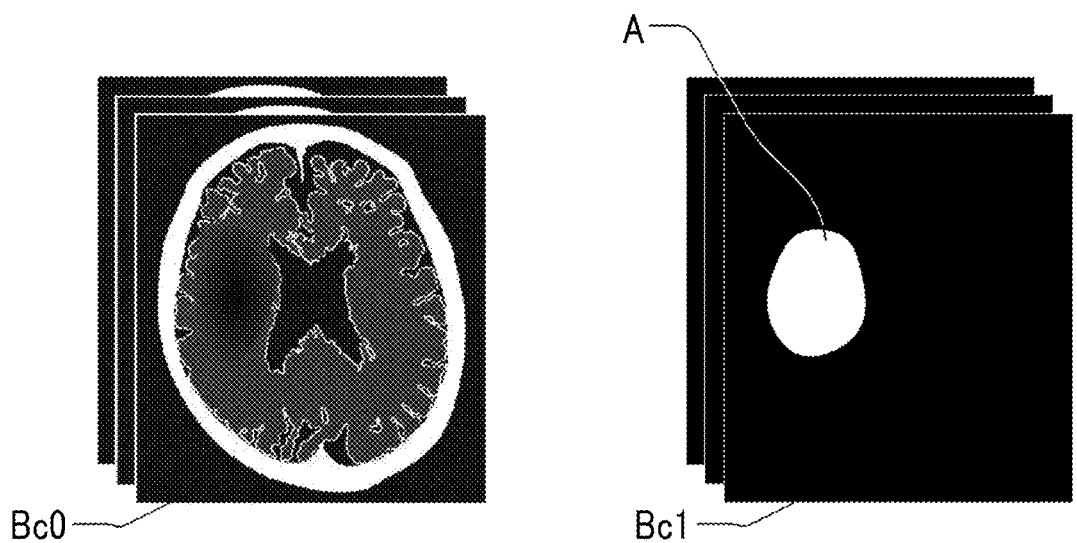
FIG. 16 is a diagram for describing the first supervised data including the CT image and a correct mask as a pair.

In addition, in the exemplary embodiments described above, the first supervised data D is the supervised data including the CT image Bc0 and the correct information J0 as a pair, and the second supervised data F is the supervised data including the variation CT image Bc2 and the correct information J2 as a pair. However, the technology of the present disclosure is not limited to this. FIG. 16 is a diagram for describing the first supervised data D-2 including the CT image Bc0 and a correct mask Bc1 as a pair. As shown in FIG. 16, the first supervised data D is supervised data including the CT image Bc0 which is the learning image for learning the learning model 22, and the correct mask Bc1 in which an infarcted region A is defined as the correct region in the CT image Bc0 as a pair.

Note that in FIG. 16, the correct mask Bc1 is defined by drawing by filling the infarcted region A, which is the correct region, with white, but the correct mask Bc1 is not limited to this. For example, the infarcted region A may be defined by drawing a boundary of the infarcted region A in white without filling the inside of the infarcted region A. In addition, the infarcted region A may be drawn in a color other than white. In addition, the infarcted region A may be defined by forming an image in which the inside of the infarcted region A and the outside of the infarcted region A are constituted by pixels having different pixel values.

The CT image Bc0 according to the present exemplary embodiment corresponds to the learning image of the present disclosure, and the correct mask Bc1 according to the present exemplary embodiment corresponds to the correct learning image of the present disclosure. Note that in a case in which the CT image Bc0 and the correct mask Bc1, that is, the first supervised data D-2 is already stored in the storage 13, the supervised data acquisition unit 21 may acquire the first supervised data D-2 from the storage 13. In addition, the supervised data acquisition unit 21 acquires the first supervised data D-2 for a large number of subjects for learning a learning model 22-2 to be described below.

In the present exemplary embodiment, the variation learning image generation unit 23 adds the variation in which the output of the learning model 22-2 deviates from the target value to the attention pixel determined by using the correct mask Bc1 in a case in which the CT image Bc0 is input to the learning model 22-2 (model shown in FIG. 17) to be described below. The learning model 22-2 will be described here. Note that a method of determining the attention pixel will be described in detail below.

Figure 17:
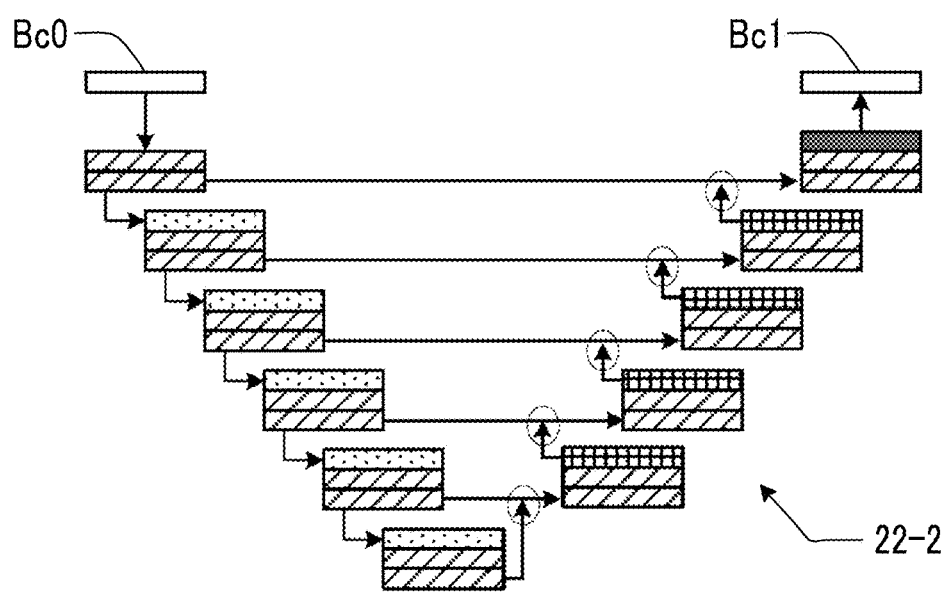
FIG. 17 is a diagram showing an example of the learning model having a U-Net structure.

The learning model 22-2 discriminates the presence or absence of the infarcted region for each pixel that constitutes the CT image Bc0. That is, the learning model 22-2 is the model for discriminating the segmentation of the CT image Bc0. Specifically, the learning model 22-2 is the model learned to output the correct mask Bc1 in which the infarcted region A is defined in the CT image Bc0 in a case in which the CT image Bc0 in which the infarcted region A is to be detected is input. In the present exemplary embodiment, the learning model 22-2 has a U Networks (U-Net) structure. The U-Net is one of fully convolution network (FCN) and is a network specialized for image segmentation. FIG. 17 is a diagram showing an example of the learning model 22-2 having the U-Net structure. In FIG. 17, a layer indicated by the diagonal line is a convolution layer, a layer indicated by a dot is a pooling layer, and a layer indicated by a grid is an up-sampling layer. In addition, in FIG. 17, a circled arrow indicates that image sizes are the same and integrated.

In the learning model 22-2, a downward path (downward arrow in FIG. 17) outputs the feature amount map in which the amount of data is reduced by a convolution process and a pooling process. On the other hand, an upward path (upward arrow in FIG. 17) is output by greatly restoring the size of the feature amount map by the convolution process and an up-sampling process. The learning model 22-2 restores the overall position information while maintaining a local feature by integrating the same image size stepwise from the deep layer in both paths. Note that the learning model 22-2 of the present exemplary embodiment can use the known U-Net structure.

In a case in which the whole x of the CT image Bc0 in which the infarcted region A is to be detected is input to the learning model 22-2, the learning model 22-2 is learned to output the correct mask Bc1 in which the infarcted region A is defined in the CT image Bc0. The correct mask Bc1 has the output value of whether each pixel that constitutes the CT image Bc0 is the pixel belonging to the infarcted region or the pixel belonging to the region other than the infarcted region. For example, the output value of whether a certain attention pixel (hereinafter referred to as the attention pixel) is the pixel belonging to the infarcted region or the pixel belonging to the region other than the infarcted region is defined as an output value Ss(x). Here, Table 2 below shows examples of the output value Ss(x) and the discrimination result by the learning model 22-2.

TABLE 2

| Output value Ss(x) | Discrimination result |
|---|---|
| $0 \leq Ss(x) < 0.5$ | Pixel of region other than infarcted region |
| $0.5 \leq Ss(x) \leq 1$ | Pixel of infarcted region |

In a case in which the output value Ss(x) of the learning model 22-2 is 0 or more and less than 0.5, the discrimination is made as the pixel other than the infarcted region, and in a case in which the output value Ss(x) of the learning model 22-2 is 0.5 or more and 1 or less, the discrimination is made as the pixel of the infarcted region. That is, for example, in a case in which the CT image Bc0 is input to the learning model 22-2, in a case in which the output value Ss(x) of the attention pixel of the learning model 22-2 is 0.6, the attention pixel is the pixel belonging to the infarcted region. In addition, for example, in a case in which the CT image Bc0 is input to the learning model 22-2, in a case in which the output value Ss(x) of the attention pixel of the learning model 22-2 is 0.3, the attention pixel is the pixel belonging to the region other than the infarcted region.

The variation learning image generation unit 23 generates the variation CT image Bc2 by adding the variation in which the output of the attention pixel of the learning model 22-2 deviates from the target value to the pixel value of the attention pixel in a case in which the CT image Bc0 is input to the learning model 22-2. For example, for the CT image Bc0 before the variation, in a case in which the output value Ss(x) of the attention pixel of the learning model 22-2 is 0.6, it is discriminated that the attention pixel is the pixel belonging to the infarcted region. Therefore, "1", which is the output value Ss(x) discriminated to have the highest possibility of the value belonging to the infarcted region in the attention pixel, is the "target value". Therefore, the "variation deviating from the target value" is the variation added to the pixel value having a value at which the output value Ss(x) of the attention pixel of the learning model 22-2 further deviates from "1" (less than "1"), the value being 0.5 or more and less than 0.6. On the other hand, for the CT image Bc0 before the variation, in a case in which the output value Ss(x) of the attention pixel of the learning model 22-2 is 0.3, it is discriminated that the attention pixel is the pixel belonging to the region other than the infarcted region. Therefore, "0", which is the output value Ss(x) discriminated to have the highest possibility of the value belonging to the region other than the infarcted region in the attention pixel, is the "target value". Therefore, the "variation deviating from the target value" is the variation added to the pixel value having a value at which the output value Ss(x) of the attention pixel of the learning model 22-2 further deviates from "0", the value being more than 0.3 and less than 0.5.

Specifically, the variation learning image generation unit 23 acquires a gradient Ms(x) of the output value Ss(x) of the learning model 22-2 with respect to an attention pixel s in a case in which the CT image Bc0 is first input to the learning model 22-2. The gradient Ms(x) of the output value Ss(x) of the learning model 22-2 with respect to the attention pixel s is derived by Expression (3).

$$Ms(x) = \partial Ss(x) / \partial x \qquad (3)$$

Note that the gradient Ms(x) can be described in the same manner as the gradient M(x) described with reference to FIG. 5, and thus the detailed description thereof will be omitted here.

Next, by using the gradient Ms(x) derived from Expression (3), the variation CT image Bc2 is generated by adding the variation to at least one pixel that constitutes the CT image Bc0 in accordance with Expression (4).

$$xa = x - k \times Ms(x) \qquad (4)$$

Note that a fixed number is k>0.

Here, x indicates the whole of the CT image Bc0, and xa indicates the whole variation CT image Bc2 after the CT image Bc0 is varied. In addition, k x Ms(x) represents the whole gradient image as in the right figure of FIG. 5.

The variation learning image generation unit 23 generates the variation CT image Bc2 in which the variation is added to at least one pixel that constitutes the CT image Bc0 by subtracting the whole gradient image k×Ms(x) from the whole x of the CT image Bc0.

Figure 18:
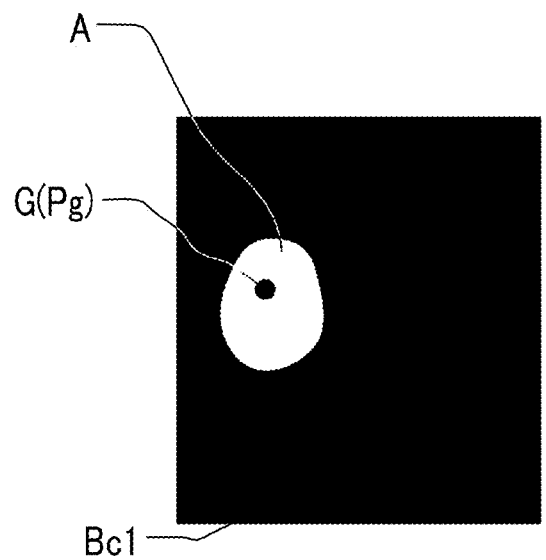
FIG. 18 is a diagram for describing an attention pixel.

Next, the method of determining the attention pixel by the variation learning image generation unit 23 will be described. The variation learning image generation unit 23 first detects the pixel to which a centroid G of the infarcted region A defined in the correct mask Bc1 belongs. FIG. 18 is a diagram for describing the attention pixel.

Figure 19:
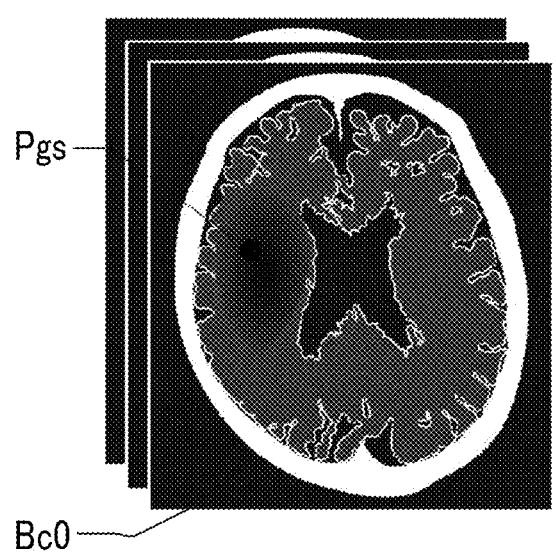
FIG. 19 is a diagram for describing the attention pixel on the CT image.

As shown in FIG. 18, the variation learning image generation unit 23 derives the centroid G of the infarcted region A. Here, the centroid G can be derived by a known method. The variation learning image generation unit 23 detects a pixel Pg to which the centroid G of the infarcted region A belongs. Next, the pixel to which the detected pixel Pg corresponds in the CT image Bc0 is determined as an attention pixel Pgs. FIG. 19 is a diagram for describing the attention pixel Pgs on the CT image Bc0.

As shown in FIG. 19, the variation learning image generation unit 23 determines the pixel on the CT image Bc0 corresponding to the pixel Pg to which the centroid G of the infarcted region A detected in the correct mask Bc1 belongs as the attention pixel Pgs. Moreover, as described above, in a case in which the CT image Bc0 is input to the learning model 22-2 (model shown in FIG. 17), the variation in which the output of the attention pixel Pgs of the learning model 22-2 deviates from the target value is added as described above. As a result, the variation learning image generation unit 23 generates the variation CT image Bc2 in which the variation is added on the CT image Bc0.

Figure 20:
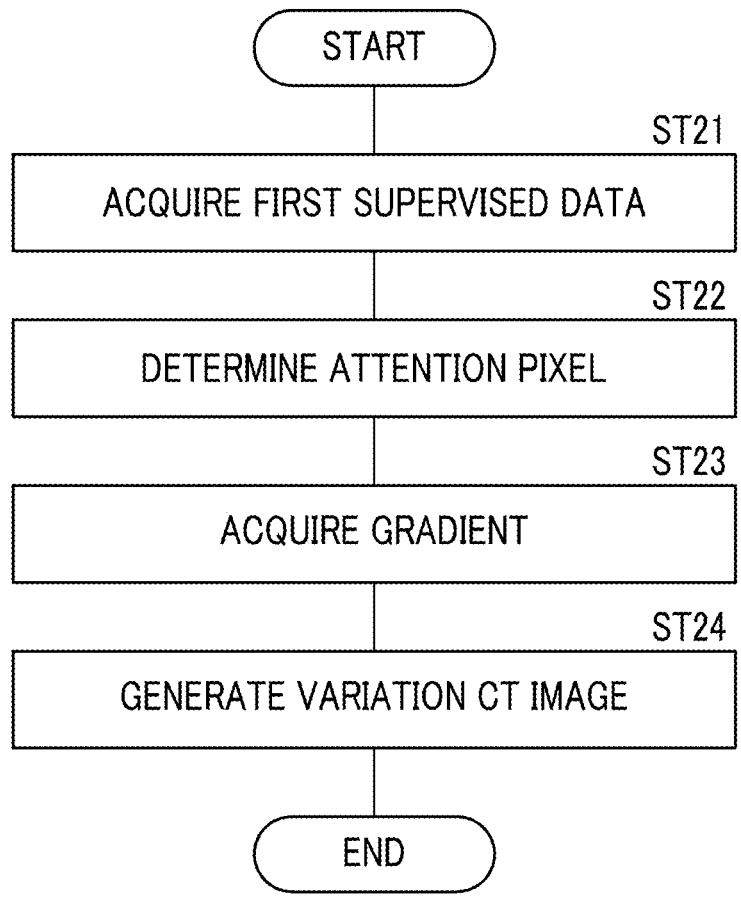
FIG. 20 is a flowchart showing the process of generating the variation CT image.

Next, a process of generating the variation CT image Bc2 according to the present exemplary embodiment will be described. FIG. 20 is a flowchart showing the process of generating the variation CT image Bc2. First, the supervised data acquisition unit 21 acquires the first supervised data D including the CT image Bc0 and the correct mask Bc1 as a pair (step ST21). Next, the variation learning image generation unit 23 determines the attention pixel Pgs in the CT image Bc0 (step ST22). Next, the variation learning image generation unit 23 acquires the gradient Ms(x) of the output value Ss(x) of the learning model 22-2 with respect to the attention pixel Pgs of the CT image Bc0 (step ST23). Moreover, the variation learning image generation unit 23 generates the variation CT image Bc2 by adding variation in which the output of the attention pixel Pgs deviates from the "target value" to the CT image Bc0 as described above (step ST24), and terminates a series of processes.

With the learning image generation device of the present exemplary embodiment, which is configured by the image acquisition unit 20, the supervised data acquisition unit 21, and the variation learning image generation unit 23, the learning image generation method of the present exemplary embodiment, and the learning image generation program of the present exemplary embodiment, by adding the variation in which the output of the attention pixel Pgs deviates from the "target value" to the CT image Bc0, it is possible to generate the variation CT image Bc2, which is difficult for the learning model 22-2 to correctly recognize the infarcted region as compared with the CT image Bc0 before the variation. As a result, the variation CT image Bc2, which is the CT image other than the limited CT image Bc0, can also be used as the learning image. Therefore, by using the limited CT image Bc0, the learning model 22-2 to be described below can be learned to be stably operated for an unknown CT image other than the CT image Bc0.

Note that in the present exemplary embodiment, the number of the attention pixel Pgs is one, but the technology of the present disclosure is not limited to this, and a plurality of the attention pixel Pgs may be used. In this case, the pixel Pg detected by the correct mask Bc1 is not limited to the pixel to which the centroid G belongs, and can be optionally detected from the pixel belonging to the infarcted region A. Moreover, in a plurality of the attention pixels Pgs1, Pgs2, on the CT image Bc0 corresponding to a plurality of the detected pixels Pg, the gradients Ms1($x$), Ms2($x$), of the output values Ss1($x$), Ss2($x$), of the learning model 22-2 are acquired.

Moreover, by using the acquired gradients Ms1($x$), Ms2($x$), the variation CT image Bc2 to which the variation is added by Expression (5) is generated.

$$xa = x - k \times (Ms1(x) + Ms2(x) + )$$  (5)

Note that a fixed number is k>0.

The variation learning image generation unit 23 generates the variation CT image Bc2 added with the variation in which the outputs of the plurality of attention pixels Pgs1, Pgs2, that constitute the CT image Bc0 deviate from the "target value" by subtracting the whole gradient image k×(Ms1($x$)+Ms2($x$)+) from the whole x of the CT image Bc0. In this way, by adding the variation in which the outputs of the plurality of attention pixels Pgs1, Pgs2, of the CT image Bc0 deviate from the "target value" to the CT image Bc0, it is possible to generate the variation CT image Bc2, which is difficult for the learning model 22 to correctly recognize the infarcted region as compared with the CT image Bc0 before the variation.

Note that in the present exemplary embodiment, the pixel Pg detected by the correct mask Bc1 is detected from the pixel belonging to the infarcted region A, but the technology of the present disclosure is not limited to this, and the pixel Pg may be detected from both the pixel belonging to the infarcted region A and the pixel belonging to the region other than the infarcted region A. In addition, the pixel Pg may be detected only from the pixel belonging to the region other than the infarcted region A.

Figure 21:
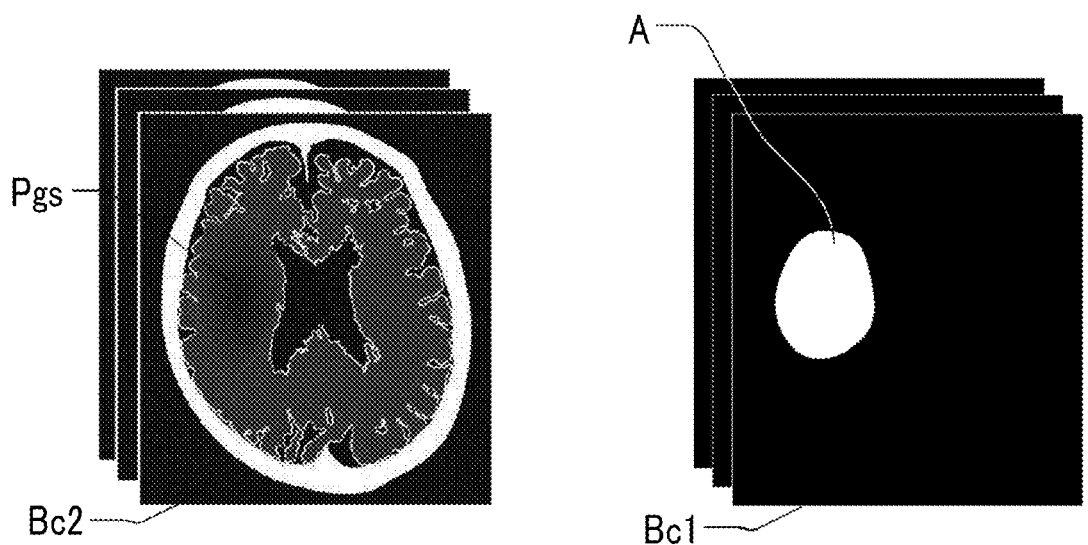
FIG. 21 is a diagram for describing the second supervised data including the variation CT image and the correct mask as a pair.

Next, the learning unit 24 learns the learning model 22-2 by using one or more first supervised data D-2 and one or more second supervised data F-2, which are acquired by the supervised data acquisition unit 21. FIG. 21 is a diagram for describing the second supervised data F-2 including the variation CT image and a correct mask as a pair. As shown in FIG. 21, the second supervised data F-2 is the supervised data including the variation CT image Bc2 and the correct mask Bc1 in which the infarcted region A is defined in the CT image Bc0 before the variation of the variation CT image Bc2 as a pair. Note that in the present exemplary embodiment, the second supervised data F-2 is the supervised data including the variation CT image Bc2 and the correct mask Bc1 in which the infarcted region A is defined in the CT image Bc0 before the variation of the variation CT image Bc2 as a pair, but may be the supervised data including the variation CT image Bc2 and a correct mask Bc3 in which the infarcted region A is newly defined in the variation CT image Bc2 as a pair. Note that the variation CT image Bc2 is varied such that the discrimination result based on the value of the output value Ss(x) of the learning model 22-2 with respect to the attention pixel s is not changed in the CT image Bc0 before the variation, and thus the correct mask Bc1 and the correct mask Bc3 in which the infarcted region A is newly defined in the variation CT image Bc2 are the same correct mask.

Figure 22:
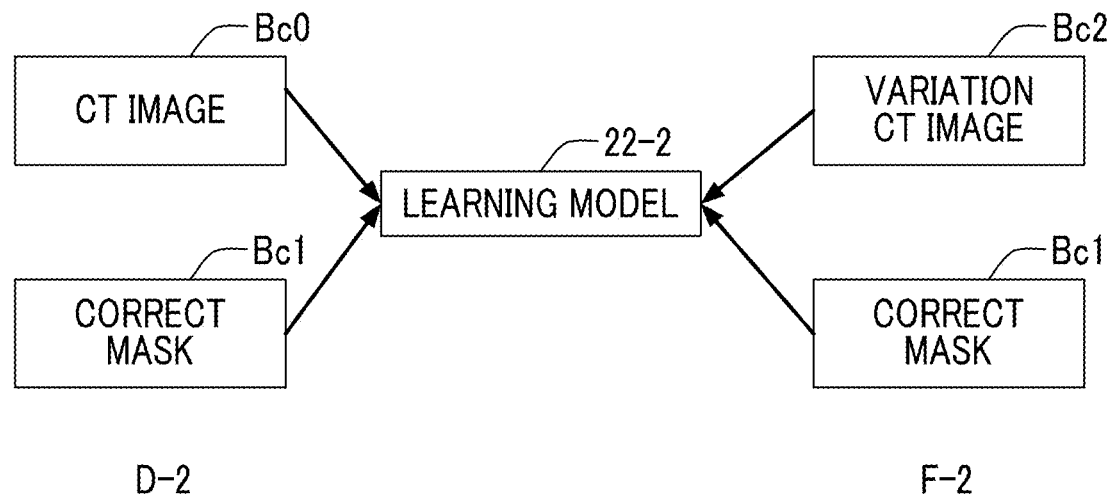
FIG. 22 is a diagram for describing the learning model.

FIG. 22 is a diagram for describing the learning method of the learning model 22-2. Note that in the present exemplary embodiment, the learning model 22-2 corresponds to the model according to the present disclosure. As shown in FIG. 22, the learning unit 24 inputs the first supervised data D-2, that is, the CT image Bc0 and the correct mask Bc1 to a learning model 22-2 to cause the learning model 22-2 to learn the infarcted region A in the CT image Bc0. As a result, in a case in which the CT image Bc0 is input, the learning model 22-2 is learned to output a region matching the correct mask Bc1 is output as the infarcted region A. In addition, the learning unit 24 inputs the second supervised data F-2, that is, the variation CT image Bc2 and the correct mask Bc1 to a learning model 22-2 to cause the learning model 22-2 to learn the infarcted region A in the variation CT image Bc2. As a result, in a case in which the variation CT image Bc2 is input, the learning model 22-2 is learned to output a region matching the correct mask Bc1 is output as the infarcted region A.

Note that a series of processes of the learning method of the present exemplary embodiment is the same processes as the flowchart shown in FIG. 11, and thus the detailed description thereof will be omitted here.

Figure 23:
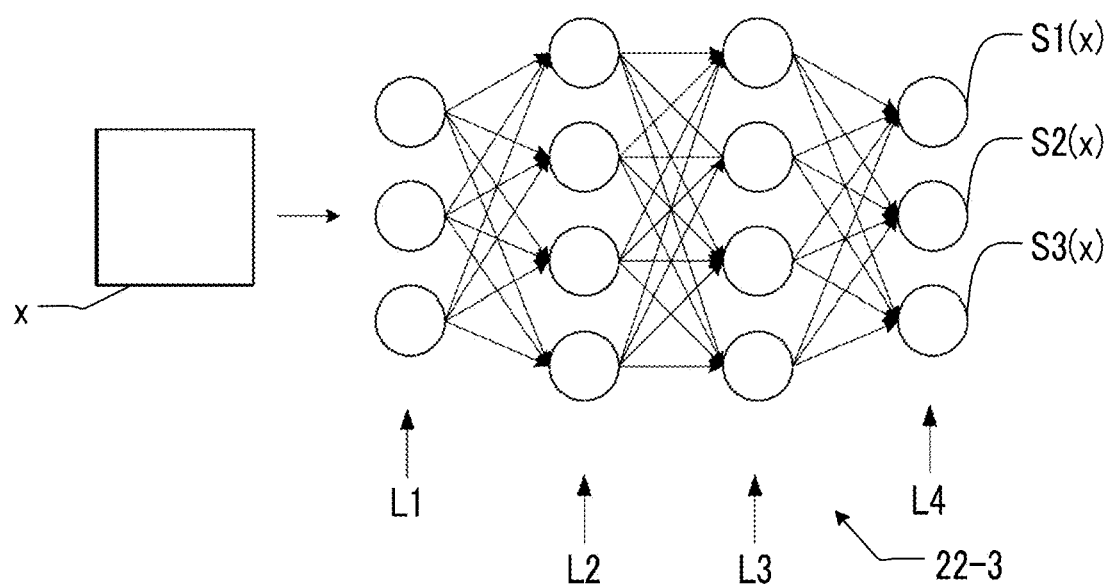
FIG. 23 is a diagram showing an example of the learning model of multi class classification.

Note that in the exemplary embodiments described above, the learning model 22 and the learning model 22-2 are single-class models having one output unit, but the technology of the present disclosure is not limited to this, and the learning models may be multi class models including a plurality of the output units. FIG. 23 is a diagram showing an example of a learning model 22-3 of multi class classification.

While the output unit L4 of the learning model 22 shown in FIG. 4 has one output layer, in the learning model 22-3 of the present exemplary embodiment, as shown in FIG. 23, the output unit L4 has three output layers. The output values $S1(x)$ to $S3(x)$ output from the three output layers include at least one of the convolution layer or the pooling layer, as in the learning model 22 shown in FIG. 4.

In the present exemplary embodiment, for example, as the output value $S1(x)$, the value indicating the discrimination result of whether or not there is the infarcted region A on the CT image Bc0 is output. As the output value $S2(x)$, a value indicating the discrimination result of an anatomical site of the infarction specified on the CT image Bc0 is output. As the output value $S3(x)$, a value indicating the discrimination result of whether or not there is a bleeding region on the CT image Bc0 is output. In the learning model 22-3 configured in this way, the gradients $M1(x)$ to $M3(x)$ are derived for each of the output values $S1(x)$ to $S3(x)$ of the input CT image Bc0 by Expressions (6) to (8).

$$M1(x) = \partial S1(x)/\partial x \qquad (6)$$

$$M2(x) = \partial S2(x)/\partial x \qquad (7)$$

$$M3(x) = \partial S3(x)\partial x \qquad (8)$$

By using the gradients $M1(x)$ to $M3(x)$ derived from Expressions (6) to (8), the variation CT image Bc2 is generated in the same manner as in the exemplary embodiments described above. Note that a process after the gradients $M1(x)$ to $M3(x)$ are derived is the same as that of the first exemplary embodiment, and thus the detailed description thereof will be omitted here.

Figure 24:
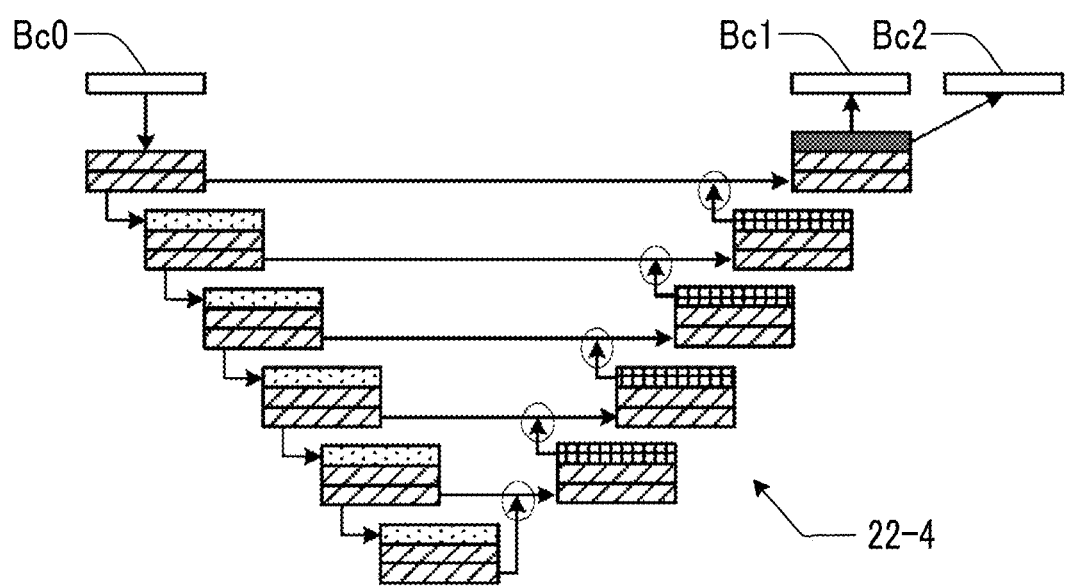
FIG. 24 is a diagram showing an example of the learning model of the multi class classification.

In addition, in the technology of the present disclosure, the learning model of the multi class classification is not limited to the learning model 22-3 shown in FIG. 23. FIG. 24 is a diagram showing an example of a learning model 22-4 of the multi class classification. The learning model 22-4 is the model learned to output the correct masks Bc1 and Bc2 in which each of the infarcted region A1 and a bleeding region A2 in the CT image Bc0 is defined in a case in which the CT image Bc0 is input. In the present exemplary embodiment, the learning model 22-4 has the U Networks (U-Net) structure.

In the learning model 22-4 as well, each of the correct masks Bc1 and Bc2 is used to calculate each of the attention pixels Pg10 and Pg20 and derive the gradients $M1(x)$ and $M2(x)$ by Expressions (6) and (7). By using the gradients $M1(x)$ and $M2(x)$ derived from Expressions (6) and (7), the variation CT image Bc2 is generated in the same manner as in the exemplary embodiments described above. Note that a process after the gradients $M1(x)$ and $M2(x)$ are derived is the same as that of the exemplary embodiments described above, and thus the detailed description thereof will be omitted here.

Note that in the exemplary embodiments described above, the gradient $M(x)$ is used for adding the variation in which the output of the learning model deviates from the target value to the pixel value of at least one pixel that constitutes the CT image Bc0 in a case in which the CT image Bc0 is input to the learning model. However, the technology of the present disclosure is not limited to this. It is not necessary to use the gradient $M(x)$ as long as the variation in which the output of the learning model deviates from the target value is added to at least one pixel that constitutes the CT image Bc0.

In addition, in the exemplary embodiments described above, the disease is the infarction, but the technology of the present disclosure is not limited to this, and for example, the disease may be bleeding or the like.

In addition, in the exemplary embodiments described above, the CT image is used as the learning image of the present disclosure, the technology of the present disclosure is not limited to this, and the learning image according to the present disclosure may be another medical image, such as the PET image, the ultrasound image, and the MRI image. The MM image may be any image of a T1 image, a T2 image, or a diffusion emphasis image.

In addition, in the exemplary embodiments described above, the brain image is used as the medical image, but the technology of the present disclosure is not limited to this. For example, the present disclosure can also be applied to discriminate the diseased region and a region of interest included in the medical images of chest, abdomen, whole body, limbs, and the like of the human body.

In addition, in the exemplary embodiments described above, the learning device 1 encompasses the learning image generation device, but the technology of the present disclosure is not limited to this, and the learning image generation device may not be encompassed. Note that in this case, the learning device 1 shall comprise the supervised data acquisition unit 21, and the supervised data acquisition unit 21 need only acquire the second supervised data including the variation learning image generated by an external learning image generation device.

In addition, in the exemplary embodiments described above, the learning models 22-2 and 22-4 have the U-Net structure, but the technology of the present disclosure is not limited to this. A fully convolution network (FCN) may be used instead of the U-Net. Note that in a case in which a model for learning a segmentation problem by the end-to-end deep learning, it can be widely applied without being limited to the U-Net and the FCN.

In addition, in the exemplary embodiments described above, for example, various processors shown below can be used as the hardware structures of processing units that execute various processes, such as the image acquisition unit 20, the supervised data acquisition unit 21, the learning model 22, the variation learning image generation unit 23, the learning unit 24, and the display control unit 25. As described above, various processors include, in addition to the CPU, which is a general-purpose processor which executes software (program) and functions as various processing units, a programmable logic device (PLD) which is a processor whose circuit configuration can be changed after manufacture, such as a field programmable gate array (FPGA), and a dedicated electric circuit which is a processor having a circuit configuration which is designed for exclusive use in order to execute a specific process, such as an application specific integrated circuit (ASIC).

One processing unit may be configured by one of various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is a form in which one processor is configured by a combination of one or more CPUs and software and this processor functions as the plurality of processing units. Second, as represented by a system on chip (SoC) or the like, there is a form of using a processor that realizes the function of the whole system including the plurality of processing units with one integrated circuit (IC) chip. In this way, as the hardware structure, various processing units are configured by one or more of various processors described above.

Further, as the hardware structure of these various processors, more specifically, it is possible to use an electrical circuit (circuitry) in which circuit elements such as semiconductor elements are combined.

The disclosure of JP 2019-138235 filed on Jul. 26, 2019 is incorporated in the present specification by reference in its entirety.

All of the documents, the patent applications, and the technological standards described in the present specification are incorporated in the present specification by reference to the same extent as a case in which individual document, patent application, and technological standard are specifically and individually noted to be incorporated by reference.

What is claimed is:

1. A learning image generation device comprising:
a memory; and
a processor coupled to the memory, the processor configured to:
acquire a learning image;
acquire an output value with respect to the learning image from a learning model by inputting the learning image to the learning model; and
generate a variation learning image by adding a variation of the output value of the learning model to a pixel value of at least one pixel that constitutes the learning image in a case in which the acquired learning image is input to the learning model, wherein the variation represents an amount of the output value of the learning model deviating from a target value of the learning model.

2. The learning image generation device according to claim 1, wherein the processor is configured to acquire a gradient of an output value for the pixel value of each pixel that constitutes the learning image, and adds the variation by using the acquired gradient.

3. The learning image generation device according to claim 1, wherein the processor is configured to:
acquire supervised data including the learning image and a correct region defined in the learning image as a pair,
determines an attention pixel by using the correct region in the acquired supervised data,
acquires a gradient of an output value of the determined attention pixel, and
adds the variation by using the acquired gradient.

4. The learning image generation device according to claim 3, wherein the processor is configured to determine the pixel in the learning image corresponding to a pixel belonging to the correct region as the attention pixel.

5. The learning image generation device according to claim 3, wherein the processor is configured to determine the pixel in the learning image corresponding to a pixel belonging to a region other than the correct region as the attention pixel.

6. The learning image generation device according to claim 3, wherein the processor is configured to determine the pixel in the learning image corresponding to a pixel belonging to a centroid of the correct region as the attention pixel.

7. The learning image generation device according to claim 1, wherein:
the model is a model having a plurality of output units that classifies the input learning image into a plurality of classes including one or more correct classes, and
the processor is configured to acquire a gradient of an output value output from the output unit that performs classification into the correct classes.

8. A learning image generation method comprising:
acquiring a learning image;
acquiring an output value with respect to the learning image from a learning model by inputting the learning image to the learning model; and
generating a variation learning image by adding a variation of the output value of the learning model to a pixel value of at least one pixel that constitutes the learning image in a case in which the acquired learning image is input to the learning model, wherein the variation represents an amount of the output value of the learning model deviating from a target value of the learning model.

9. A non-transitory computer readable medium storing a learning image generation program causing a computer to function as:
an image acquisition unit that acquires a learning image; and
a variation learning image generation unit that acquires an output value with respect to the learning image from a learning model by inputting the learning image to the learning model and generates a variation learning image by adding a variation of the output value of the learning model to a pixel value of at least one pixel that constitutes the learning image in a case in which the learning image acquired by the image acquisition unit is input to the learning model, wherein the variation represents an amount of the output value of the learning model deviating from a target value of the learning model.

10. A learning method comprising:
learning a model by using one or more first supervised data including a learning image and correct information in the learning image as a pair, and one or more second supervised data including one or more variation learning images and the correct information in the learning image as a pair, wherein the one or more variation learning images are generated by adding a variation in which an output of the model deviates from a target value to a pixel value of at least one pixel that constitutes the learning image in a case in which the learning image is input to the model, and the output of the model is generated by inputting the learning image into the model, and the variation learning images are generated based on the output of the model.

11. The learning method according to claim 10, wherein the correct information is a correct region defined in the learning image.

12. The learning method according to claim 10, wherein:
the model is learned by using a plurality of the first supervised data in first learning, and
the model is learned by replacing at least one first supervised data among the plurality of first supervised data with the second supervised data in second and subsequent learning.

13. The learning method according to claim 10, wherein:
the model is learned by using a plurality of the first supervised data in first learning, and the model is learned by adding at least one second supervised data in second and subsequent learning.

14. The learning method according to claim 12, wherein at least one of the second supervised data to be used or the number of the second supervised data is randomly set for each learning in the second and subsequent learning.

15. The learning method according to claim 12, wherein at least one of the second supervised data to be used or the number of the second supervised data is set in advance in the second and subsequent learning.

16. The learning method according to claim 12, wherein the model is learned by using only the plurality of first supervised data at least once in the second and subsequent learning.

17. A learning device comprising:
a memory; and
a processor coupled to the memory, the processor configured to:
acquire one or more first supervised data including a learning image and correct information in the learning image as a pair, and one or more second supervised data including one or more variation learning images and the correct information in the learning image as a pair, wherein the one or more variation learning images are generated by adding a variation in which an output of a model deviates from a target value to a pixel value of at least one pixel that constitutes the learning image in a case in which the learning image is input to the model, and the output of the model is generated by inputting the learning image into the model, and the variation learning images are generated based on the output of the model; and
learn the model by using the one or more first supervised data and the acquired one or more second supervised data.

18. A learning device comprising:
a memory; and
a processor coupled to the memory, the processor configured to:
acquire one or more first supervised data including a learning image and correct information in the learning image as a pair, and one or more second supervised data including one or more variation learning images generated by adding a variation in which an output of a model deviates from a target value to a pixel value of at least one pixel that constitutes the learning image in a case in which the learning image is input to the model, and the correct information in the learning image before the variation in each of the one or more variation learning images as a pair; and
learn the model by using the one or more first supervised data and the acquired one or more second supervised data,
wherein the processor is configured to learn the model by the learning method according to claim 10.

19. A non-transitory computer readable medium storing a learning program causing a computer to function as:
a supervised data acquisition unit that acquires one or more first supervised data including a learning image and correct information in the learning image as a pair, and one or more second supervised data including one or more variation learning images and the correct information in the learning image as a pair, wherein the one or more variation learning images are generated by adding a variation in which an output of a model deviates from a target value to a pixel value of at least one pixel that constitutes the learning image in a case in which the learning image is input to the model, and the output of the model is generated by inputting the learning image into the model, and the variation learning images are generated based on the output of the model; and
a learning unit that learns the model by using the one or more acquired first supervised data and the one or more acquired second supervised data acquired by the supervised data acquisition unit.

* * * * *